US009750691B2

(12) United States Patent
McGlone et al.

(10) Patent No.: US 9,750,691 B2
(45) Date of Patent: *Sep. 5, 2017

(54) PHEROMONE COMPOSITIONS AND THEIR USE TO MODIFY BEHAVIOR IN DIFFERENT VERTEBRATE SPECIES

(71) Applicant: Sergeant's Pet Care Products, Inc., Omaha, NE (US)

(72) Inventors: John McGlone, Lubbock, TX (US); Larry Nouvel, Plano, TX (US)

(73) Assignee: Sergeant's Pet Care Products, Inc., Omaha, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/623,319

(22) Filed: Sep. 20, 2012

(65) Prior Publication Data

US 2013/0072570 A1 Mar. 21, 2013

Related U.S. Application Data

(60) Provisional application No. 61/536,673, filed on Sep. 20, 2011.

(51) Int. Cl.
| | | |
|---|---|---|
| *A61K 31/11* | (2006.01) | |
| *A61K 9/12* | (2006.01) | |
| *A61K 31/568* | (2006.01) | |
| *A61K 9/00* | (2006.01) | |
| *A61K 31/565* | (2006.01) | |
| *A61K 45/06* | (2006.01) | |
| *A61K 47/10* | (2017.01) | |

(52) U.S. Cl.
CPC .............. *A61K 9/124* (2013.01); *A61K 9/008* (2013.01); *A61K 9/12* (2013.01); *A61K 31/565* (2013.01); *A61K 31/568* (2013.01); *A61K 45/06* (2013.01); *A61K 47/10* (2013.01)

(58) Field of Classification Search
None
See application file for complete search history.

(56) References Cited

U.S. PATENT DOCUMENTS

| 5,272,134 | A | 12/1993 | Berliner | |
|---|---|---|---|---|
| 2006/0252738 | A1* | 11/2006 | Avelino et al. | 514/177 |
| 2006/0269513 | A1 | 11/2006 | Dodd | |
| 2007/0048230 | A1 | 3/2007 | Parsadayan | |
| 2007/0048231 | A1 | 3/2007 | Parsadayan | |
| 2009/0275670 | A1 | 11/2009 | Marshall | |
| 2011/0064780 | A1 | 3/2011 | Marshall | |
| 2011/0150822 | A1* | 6/2011 | Nouvel et al. | 424/84 |

FOREIGN PATENT DOCUMENTS

WO    WO 02/067693    *  9/2002

OTHER PUBLICATIONS

LeMaster et al. (Chapter 21 of Chemical Signals in Vertebrates 11, published by Springer (2008), pp. 223-230).*
Jordan, V. C. (Nature Reviews: Drug Discovery, Feb. 2003, 205-213).*
Kronen et al. ("A synthetic fraction of feline facial pheromones calms but does not reduce struggling in cats before venous catheterization," Veterinary Anaesthesia and Analgesia vol. 33, Issue 4, pp. 258-265, Jul. 2006).*
Schaal et al., Chemical and behavioral characterization of the rabbit mammary pheromone, Nature, 424:68-72, 2003.
Dr. John McGlone, The Pheromone Site, http://www.depts.ttu.edu/animalwelfare/Research/Pheromones/index.php.
Coureaud et al., "Newborn Rabbit Responsiveness to the Mammary Pheromone is Concentration-dependent", Chem. Senses 29:341-350, 2004; DOI 10.1093/chemse/bjh037.
Moncomble et al., "The Mammary Pheromone of the rabbit: from where does it come?", Animal Behaviour, 2005, 69, 29-38; doi: 10.1016/j.anbehay.2004.05.006.
Hudson et al., "Olfactory Guidance of Nipple-Search Behaviour in Newborn Rabbits", Ontogeny of Olfaction, 1986, pp. 243-254.
Swaney et al., "The evolution of pheromonal communication", Behavioural Brain Research, vol. 200, No. 2, Jun. 25, 2009, pp. 239-247.

* cited by examiner

Primary Examiner — Kortney L Klinkel
Assistant Examiner — William Lee
(74) Attorney, Agent, or Firm — Polsinelli PC

(57) ABSTRACT

A composition comprising an INTEROMONE® is described for the modification of undesirable or harmful stress-related behaviors or other behaviors or physiology in a variety of vertebrate species, as well as methods of using the compositions in vertebrates from a species different than the species in which the INTEROMONE® is a naturally occurring pheromone.

13 Claims, 20 Drawing Sheets

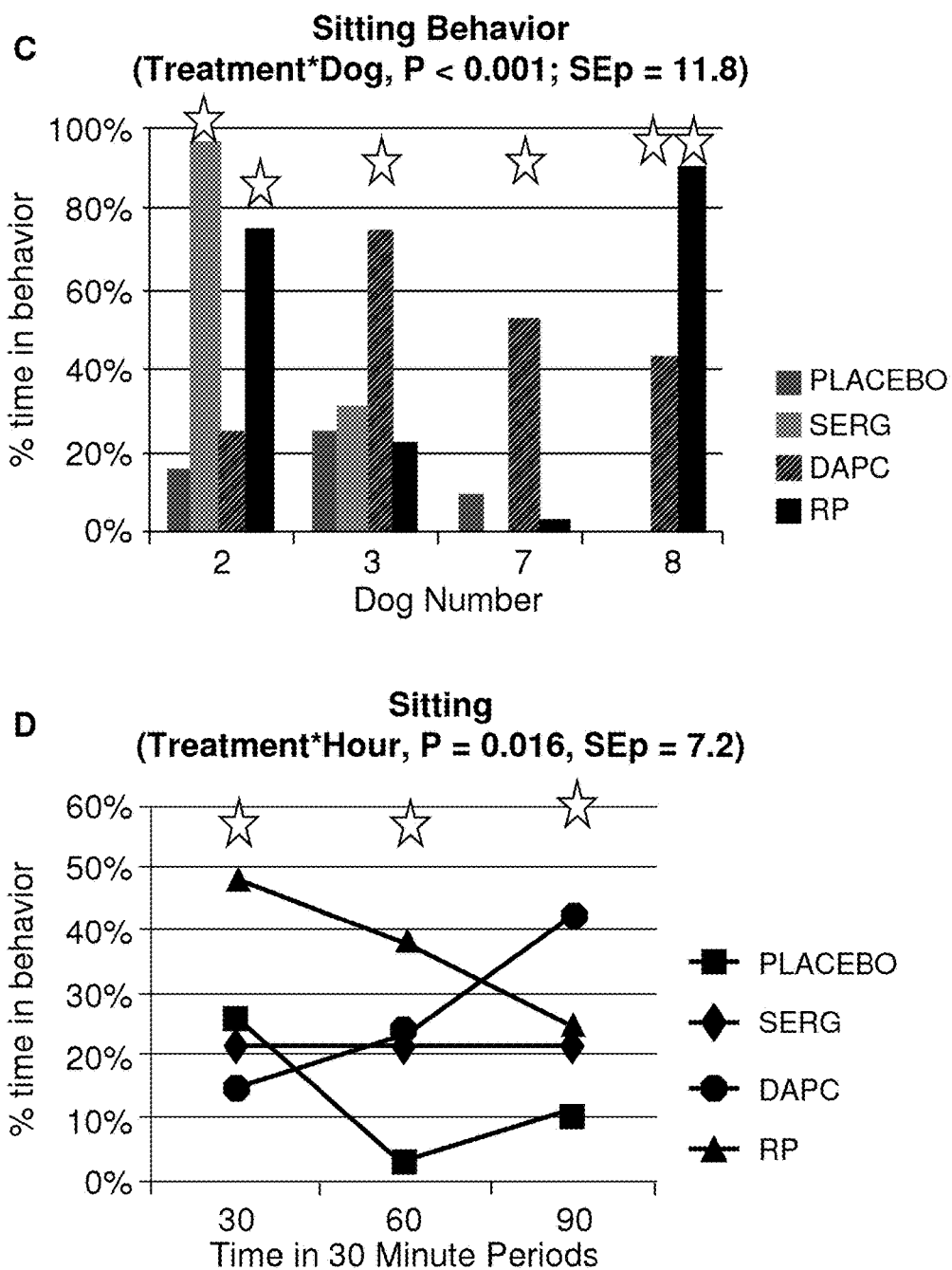

C

D

Pace-Walk Behavior, %
(Treatment*Dog, P < 0.001; SEp = 15.4%)

Standing Behavior, %
(Treatment*Dog, P < 0.03; SEp = 9.08%)

PHEROMONE COMPOSITIONS AND THEIR USE TO MODIFY BEHAVIOR IN DIFFERENT VERTEBRATE SPECIES

RELATED APPLICATION

This application relates to and claims the priority of U.S. Provisional Patent Application No. 61/536,673, which was filed Sep. 20, 2011 and is hereby incorporated by reference in its entirety.

FIELD OF THE INVENTION

The present disclosure is broadly concerned with the field of animal behavior and the use of pheromones and INTEROMONE® compositions. More particularly, the present disclosure is concerned with the use of a rabbit pheromone (2-methylbut-2-enal) as an INTEROMONE® to produce a different behavioral or physiological effect (such as a calming or behavioral-altering effect) in a different vertebrate species from which the pheromone is produced, for example, such as in dogs, cats, snakes, birds, or horses.

BACKGROUND OF THE INVENTION

Pheromones are chemicals released by living organisms that send information to other organisms of the same species via scent. Pheromones are released in response to stress, alarm, danger, sexual fertility, and in other behavioral contexts. Pheromones, by definition and according to evolutionary theory, are species-specific, that is, they are effective in eliciting an innate response only in members of the same species.

One of the best characterized mammalian pheromones is the rabbit nipple "search pheromone." Sensed by rabbit pups via their main olfactory system, the pheromone elicits a characteristic nipple search behavior that quickly results in the location of a nipple. (See Distel, H. and Hudson, R. (1985), "The contribution of the olfactory and tactile modalities to the performance of nipple-search behavior in newborn rabbits." J. Comp. Physiol. [A] 157, 599-605) This guidance cue is particularly important for rabbits, as a doe only nurses her pups for around four minutes once a day and the quick location of a nipple in the face of sibling competition is vital for survival. This "search pheromone" has recently been shown to be a single molecule, 2-methylbut-2-enal (Schaal et al., Chemical and behavioural characterization 46028352.1 of the rabbit memory pheromone, Nature, 424:68-72, 2003), which is produced in rabbit milk and is sufficient to elicit full nipple search and grasping behavior when presented on its own at concentrations as low as 10 ng/mL.

Chemicals that provide interspecies communication are called allelochemicals. Some compounds are known to be a pheromone in one species, but have been observed to have strong behavioral effects in other species. For example, chemicals produced and released by one species that affect the behavior or physiology of another species to the benefit of the originator but not the receiver are known in the art as allomones (See Grasswitz, T. R. and G. R. Jones (2002). "Chemical Ecology". Encyclopedia of Life Sciences. John Wiley & Sons, Ltd. doi:10.1038/npg.els.0001716). The production of allomones in natural environments has been mainly observed in plant species, which utilize allomones for example to protect plants against insect herbivores.

A kairomone is another known allelochemical. It is emitted by one species and benefits another species, but does not benefit and often harms the emitter. The production of kairomones in natural environments has been mainly observed in insect species. For example, the Ponderosa Pine tree produces a terpene called myrcene when the Western pine beetle damages the tree. The emission of this chemical then lures more beetles to the tree (See Wyatt, T. D. (2003). Pheromones and Animal Behaviour: Communication by Smell and Taste, First Edition (Cambridge, UK: Cambridge University Press).

A synomone is an allelochemical produced and released by one species that benefits both the emitter and receiver. For example, plants emit odors that work to attract bees. The bees are attracted to the plants to feed and then the bees take the pollen to fertilize other plants/flowers.

Accordingly, the allelochemicals known in the art involve the observation of chemicals produced by one species having an effect on another species to the benefit and/or detriment of the emitting or receiving species. What is described is an allelochemical that affects the behavior and/or physiology of another species (i.e., the receiving species) without additionally having a beneficial or harmful effect on the emitting species and having a novel or unrelated behavioral or physiological effect on the receiving species.

For instance, while domestic dogs are known to bark as part of their normal method of communication, dogs may show excessive barking/jumping/mobbing/begging in response to external cues or due to boredom. Mobbing includes repetitive barking and jumping. Certain dogs will bark and jump in an excitable manner when they hear or see people, animals, vehicles, or machines. One theory is that excessive barking is part of the "mobbing" behavior that pack animals have when they attack a prey species (Lord et al., Barking and mobbing., Behav. Processes, 81:358-368, 2009).

Methods used in the art to stop the barking/jumping/begging syndrome have included shock collars, odor sprays, and loud noises, all of which work by startling or distracting the dog from engaging in the undesirable behavior. Dog appeasing pheromones, including synthetic compositions believed to replicate certain calming pheromones emitted by dogs, have also been used in the art to treat certain behavioral problems in dogs, but to date, have not been successful in alleviating the barking/jumping syndrome exhibited by certain dogs. Moreover, the pheromones used in the art have not been directed for use with animal species other than the species from which the pheromones are emitted.

Accordingly, it would be desirable to provide methods and compositions comprising a compound known to be a pheromone in one species to positively modify animal behavioral problems in a variety of different vertebrate species. In particular, there is a need in the art for use of an INTEROMONE® to calm, sedate, reduce anxiety, or otherwise positively modify the behavior of a variety of vertebrate species, including the barking/jumping/begging syndrome exhibited by some dogs or to calm anxious dogs or cats or other vertebrate species.

SUMMARY OF THE INVENTION

It is an object of the present invention to provide novel methods and compositions for the modification of behavior in vertebrate species comprising compounds that have been isolated from one vertebrate species but, surprisingly, have the effect of modifying the behavior in a different vertebrate species. Specifically, certain pheromones have been identified which can be made into compounds and used as part of a method to have cross-species effects as INTEROMONE®.

An INTEROMONE® is any naturally secreted or synthetically produced chemical emitted as a pheromone within one species, which, when isolated and administered to a member of a different vertebrate species, elicits a change in behavior or physiology of the different species without the requirement of benefitting and/or harming the species from which the chemical is released.

The present disclosure is specifically concerned with the INTEROMONE® 2-methylbut-2-enal (as discussed, a pheromone in a rabbit's mammary system) and its use in various compositions to effect a modification of behavior in a variety of vertebrates, for example dogs, horses, cats, snakes, and birds. 2-methylbut-2-enal is a pheromone secreted by a mother rabbit to help her pups to nurse. It was surprising to learn through the present invention that 2-methylbut-2-enal has powerful effects on other species, such as dogs, and was observed to change dog behavior.

The compositions of the invention may optionally include other ingredients as necessary or desired, depending on the form and intended use of the final product. Such optional ingredients can include, but are not limited to, carriers such as water, alcohols, solvents, and the like; fragrances, coloring agents, preservatives, antioxidants, and the like. Examples of the resultant product include, but are not limited to, a spray, a diffuser, a spraying collar, or a collar. Alternatively, the resultant product may be an aerosol, a foam, a dip, a wipe, a cream, a gel, a lotion, or a fabric garment.

Another object of the present invention is to provide a method for modifying or positively affecting the behavior of a vertebrate, the method comprising administering a composition comprising an INTEROMONE®, such as 2-methylbut-2-enal, in an amount effective to affect the behavior of a particular vertebrate, wherein the vertebrate whose behavior is being modified is different than that from which the INTEROMONE® is emitted as a pheromone.

Another object of the present invention is to provide for use of a formulation comprising an INTEROMONE® to positively affect the behavior (e.g. calm) in a different vertebrate species. It is both unexpected and surprising that a chemical known to be a pheromone in one species can have a strong positive behavioral or physiological effect on members of other vertebrate species since pheromones are, by definition, functional only within a particular species.

Various objects and advantages of this use will become apparent from the following description taken in conjunction with the accompanying drawings wherein are set forth, by way of illustration and example, certain embodiments of this invention.

BRIEF DESCRIPTION OF THE DRAWINGS

FIG. 3D is a graphic representation of overall sitting behavior in dogs over a 2 hour-period in Study 1.

FIG. 10A shows all treatment groups and FIGS. 10B-D compare each treatment group with the Placebo.

FIG. 24A shows the main effects of Serg and RP collars. FIG. 24B shows the effects of Serg, RP, and Serg/RP combination collars.

DETAILED DESCRIPTION OF THE INVENTION

Figure 1:
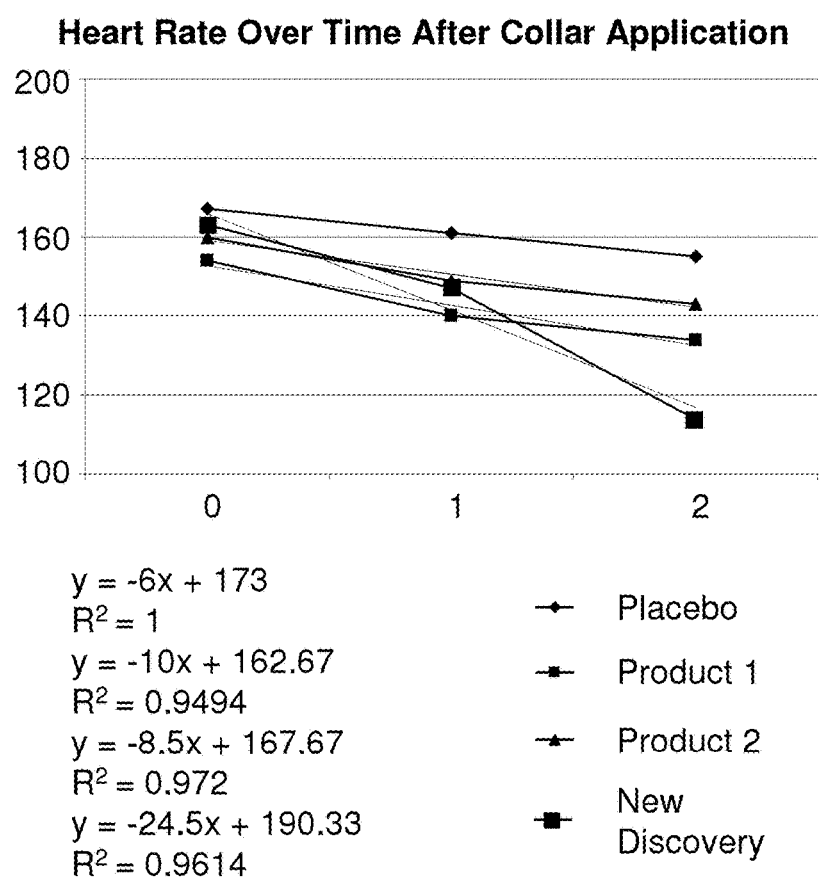
FIG. 1 is a graphic representation of a comparative test of dogs receiving treatment with current calming products available on the market (Product 1 and Product 2), a placebo, and a composition comprising 2-methylbut-2-enal (New Discovery).

The broad term, INTEROMONE®, is used herein to refer to chemicals emitted as pheromones within one vertebrate species that influence the behavior or physiology of a different species without the requirement of benefitting and/or harming the emitter or receiving species (although an INTEROMONE® could benefit or harm the emitting or receiving species). The surprising use of specific pheromones having a cross-species effect without providing any benefit or harm to the emitting species has not heretofore been developed.

The present invention relates to the use of 2-methylbut-2-enal in a composition as an INTEROMONE®, rather than as a rabbit pheromone as it is known and used in the art, in order to affect the behavior of different vertebrate species (such as, for example, dogs, cats, horses, frogs, snakes, birds, etc.). One of skill in the art will appreciate that additional pheromones not specifically disclosed herein may be found to have differential and perhaps beneficial effects in other species, such as, pheromones from other mammals (e.g., cats, tigers, lions, elephants, hamsters, mice, and rats), pheromones from reptiles (e.g., snakes and lizards), pheromones from birds, or pheromones from amphibians. 2-methylbut-2-enal has been formulated into a composition as an INTEROMONE® for administration to different species (such as, for example, the horse, dog, cat, and other vertebrates) in order to positively modify the behavior of members of the different species.

In particular, administration of 2-methylbut-2-enal as an INTEROMONE® to dogs surprisingly results in reducing activity or positively modifying the behavior of dogs that exhibit the anxious behaviors.

The present disclosure provides for a composition comprising an INTEROMONE®, which is a chemical or compound related thereto emitted by one species and known to be a pheromone within that species to modify the behavior of different vertebrate species. When the composition comprising the INTEROMONE® is applied to or in the vicinity of different vertebrate species, the animal is calmed for a period of time. It is unexpected and surprising that a natural compound found in one vertebrate species can have a large, meaningful effect on members of another vertebrate species since pheromones are, by definition, species-specific. Androstenone (as disclosed in U.S. application Ser. No. 13/623,279, filed on Sep. 20, 2012) and 2-methylbut-2-enal are two examples that work in a cross-species manner. Other chemicals and their cross-species beneficial use may become apparent to those skilled in the art following the teachings of the present invention.

I. Formulations

The formulations of the present invention may comprise a chemical that is naturally secreted, isolated from a secretion, or synthetically duplicated from a vertebrate species. The chemicals that may be used in accordance with the present invention are those that produce a certain effect within the species from which they are secreted and a different effect when used in another species.

The formulations of the present invention comprise an INTEROMONE®. In a preferred embodiment, 2-methylbut-2-enal is used as an INTEROMONE®. The 2-methylbut-2-enal used in the compositions may be the natural pheromone secreted or isolated directly from a rabbit, or a synthesized compound characterized by the following structural formula (including enantiomers, diastereomers, or racemates thereof):

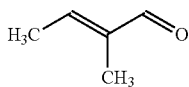

Formula I

The amount of 2-methylbut-2-enal in the formulation will be an amount effective to positively modify or alter the behavior (e.g., calm, reduce nervousness, or lower the heart rate) of a particular animal. Generally, the amount of 2-methylbut-2-enal in the formulation should be at least 0.001% (w/w) of the total composition. In one embodiment, the concentration of 2-methylbut-2-enal in the composition ranges from between about 0.001% to about 1% (w/w). In another embodiment, the concentration of 2-methylbut-2-enal in the composition ranges from between about 0.01% to about 0.1% (w/w). Preferably, the concentration of 2-methylbut-2-enal present in the composition ranges from between about 0.01% to about 0.05% (w/w) and most preferably the concentration of 2-methylbut-2-enal in the composition is about 0.01% (w/w).

In one embodiment, the composition of the present invention contains 2-methylbut-2-enal. In another embodiment, the composition contains a combination of 2-methylbut-2-enal and at least one additional pheromone composition. For instance, the composition may comprise 2-methylbut-2-enal and at least one additional pheromone composition, such as the composition described in U.S. Publication No. 2011/0150822.

In addition to an INTEROMONE®, the formulations may optionally contain additional components such as solvents, propellants, surface-active agents, thickeners, and fragrances (i.e., "additional components"). The formulation may include one additional component or a combination of any of the forgoing additional components in varying amounts. Suitable examples of each type of additional component are detailed below.

In a preferred embodiment, the formulation includes at least one carrier solvent. Suitable carrier solvents are generally known within the art and are recognized to include lipophilic organic diluents, alcohols, ethylene glycol, propylene glycol, dipropylene glycol, ether, chloroform, benzene, carbon disulfide, oils including non-volatile and volatile liquids and oils, water, and combinations thereof. For example, an INTEROMONE® can be dissolved in a suitable alcohol and supplied in a liquid form such as a pump spray or for use in a plug-in diffuser. Suitable alcohols include ethanol, propanol, isopropanol, butanol, pentanol, hexanol, heptanol, octanol, and phenyl ethyl alcohol. In a preferred embodiment, the alcohols comprise ethanol, isopropanol, butanol, and phenyl ethyl alcohol. An alcohol solvent can be combined with water or a lipophilic organic diluent or carrier such as ethylene glycol, propylene glycol, dipropylene glycol, dipropylene glycol monoethyl ether, dipropylene glycol methyl ether, or Dow Corning® Q7-9180 silicone liquid. In a preferred embodiment, the solvent is a combination of water and an alcohol selected from the group consisting of ethanol or isopropanol. In a one embodiment, the amount of solvent present in the composition ranges from between about 0.5% and 99.99% (w/w) of the composition. Preferably, the amount of water present in the composition ranges from between about 70% and about 99.99% (w/w) of the composition and most preferably ranges from between about 80% and about 98.5% (w/w). Preferably the amount of alcohol present in the composition ranges from between about 1% and about 20% (w/w) and most preferably ranges from between about 1.5% and about 10% (w/w).

The formulation may additionally include a propellant. Suitable propellants include chlorofluorocarbons (CFC) such as trichloromonofluoromethane, dichlorodifluoromethane, and dichlorotetrafluoroethane; hydrochlorofluorocarbons (HCFC) or hydrofluorocarbons (HFC) such as chlorodifluoromethane, trifluoromonofluoroethane, chlorodifluoroethane, difluoroethane, and heptafluoropropane; hydrocarbons such as propane, butane, and isobutene; and compressed gases such as nitrogen, carbon dioxide, and nitrous oxide, as well as combinations of any of the above described propellants. In one embodiment, the propellant is propane. In another embodiment, the propellant is 1,1-difluoroethane. The propellant does not comprise an inert gas of Tumorigen compound class, which includes 1,1,1,2-tetrafluoroethane, chlorodifluoromethane, and dichlorodifluoromethane. Preferably, the propellant has a flash point of less than about −50° C. Generally, when a propellant is included in the composition, such will range from between about 75% to about 99.99% (w/w) of the composition, preferably between about 85% and about 99.99% (w/w), and most preferably from between about 95% and about 99.99% (w/w).

The formulation may optionally include one or more surface-active agents (also called surfactants). Surfactants are generally used in preparing those embodiments of the present invention directed to compositions that are formulated as emulsions. Either water in oil or oil in water emulsions may be formulated. Examples of suitable surfactants include: nonionic ethoxylated and nonethoxylated surfactants, abietic acid, almond oil PEG, beeswax, butylglucoside caprate, C18-C36 acid glycol ester, C9-C15 alkyl phosphate, caprylic/capric triglyceride PEG-4 esters, ceteareth-7, cetyl alcohol, cetyl phosphate, corn oil PEG esters, DEA-cetyl phosphate, dextrin laurate, dilaureth-7 citrate, dimyristyl phosphate, glycereth-17 cocoate, glyceryl erucate, glyceryl laurate, hydrogenated castor oil PEG esters, isosteareth-11 carboxylic acid, lecithin, lysolecithin, nonoxynol-9, octyldodeceth-20, palm glyceride, PEG diisostearate, PEG stearamine, poloxamines, polyglyceryls, potassium linoleate, PPG's, raffinose myristate, sodium caproyl lactylate, sodium caprylate, sodium cocoate, sodium isostearate, sodium tocopheryl phosphate, steareths, TEA-C12-C13 pareth-3 sulfate, tri-C12-C15 pareth-6 phosphate, and trideceths.

In certain applications, it may be desirable to thicken the formulation. Suitable examples of thickening or viscosity increasing agents, include agents such as: acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxytheylcellulose, hydroxypropylcellulose, hydroxpropyl starch, isopropyl palmitate, magnesium alginate, methylcellulose, microcrystalline cellulose, pectin, various PEG's, polyacrylic acid, polymethacrylic acid, polyvinyl alcohol, various PPG's, sodium acrylates copolymer, sodium carrageenan, xanthan gum, and yeast beta-glucan. The amount of thickener present in the formulation may range from between about 1% to about 30% (w/w), preferably from between about 5% to about 20% (w/w), and most preferably from between about 10% to about 15% (w/w).

The composition may additionally comprise a fragrance. The fragrance may be any fragrance that provides a desired odor masking effect since a particular INTEROMONE® may have a pungent odor. Although a variety of fragrances may be employed without departing from the scope of the present invention, suitable fragrances include floral essences, citrus blossoms, oil or extracts of conifers, or spices. Examples of floral essences include rose, lilac, lavender, gardenia, and jasmine. Suitable citrus blossoms include orange and lemon, and suitable oil or extracts of conifers include pine and juniper. Generally, fragrance may comprise between about 0.25% and about 1% (w/w) of the composition.

II. Routes of Administration

Mammals, including dogs, have several anatomical organs that receive olfactory signals. The two most dominant "smell" organs are the main olfactory epithelium (MOE) and the vomeronasal organ (VNO). Other sensory fibers are in the nasal cavity that can sense odors, but the main olfactory bulb and accessory olfactory bulb (receiving signals from the VNO) are the major integrating systems.

The olfactory bulb lies at the front of the brain. It sends neuronal projections through a bone and extends these projections into the olfactory epithelium. The MOE is an extensive area with a rich blood supply and mucosa in which odor aerosol molecules pass on their way to the lungs. Odor or water droplets will settle on the MOE, and if an odor receptor is present, that odor receptor will be bound and cause activation of the sensory neurons. Among all the genes in the mammalian body, the olfactory receptors have the largest number of genes. This indicates the importance of olfactory communication in animals, some of which seems to be lost in humans.

Administration of the INTEROMONE® composition to a subject animal is typically accomplished through any method allowing for delivery of an effective amount of the INTEROMONE® via inhalation by the animal. Such methods of administration include, for example, placing or distributing the composition comprising the INTEROMONE® in the environment of the animal, either by incorporating the composition into a wearable device such as a collar, or by applying (e.g. spraying or wiping) the composition to surfaces in the living environment of the animal or directly onto the animal, such as to its facial region or head. For example, the INTEROMONE® composition may be administered topically to an animal using an aerosol, pump spray, foam, collar, wipe, dip, liquid, gel, lotion, and/or cream. The term "effective amount" describes an amount of INTEROMONE® present in a composition that is sufficient to produce a noticeable modification, i.e. improvement, of animal behavior in the subject animal, as determined according to behavioral observations as described herein. The effective amount will depend on factors such as the severity of the behavior being treated; individual animal parameters including age, physical condition, size and weight; concurrent treatments; the frequency of treatment; or the mode of administration. These factors are well known to those of ordinary skill in the art and can be addressed with no more than routine experimentation.

In one embodiment, the INTEROMONE® can be incorporated in various ways as are generally well known into a solid carrier material to form a collar or tag, and the collar or tag is then worn by the animal. The solid carrier material is selected from among those materials, typically polymeric compounds, generally recognized to be suitable for release of active compounds and set forth in further detail herein below. Alternatively, the INTEROMONE® can be combined with a solvent to form a liquid solution and the liquid solution can be further prepared in various formulations suitable for delivery to the animal by inhalation. For example, liquid solutions can be further prepared according to methods well known in the art such as a pump spray, aerosol, gel, foam, shampoo, dip, cream, lotion, gel, diffuser, or spot-on formulation.

In a preferred embodiment, 2-methylbut-2-enal is dissolved or diluted in a nonaqueous organic solvent or solvent mixture to form a solution for incorporation into a pump spray containing the INTEROMONE®. The solution may optionally be combined with at least one additional pheromone/INTEROMONE® or pheromone/INTEROMONE® composition. A preferred pump spray solution will comprise about 0.01% (w/w) 2-methylbut-2-enal, about 10% (w/w) isopropyl alcohol and about 89% (w/w) water. Additionally, between about 0.5% and 1% (w/w) of a fragrance may be added to the solution.

In a further embodiment, 2-methylbut-2-enal is dissolved or diluted with a solvent and a thickener to form a solution for use in a diffuser. The solution may optionally be combined with at least one additional pheromone/INTEROMONE® or pheromone/INTEROMONE® composition. A preferred diffuser solution will comprise about 0.02% (w/w) 2-methylbut-2-enal, between about 80% to about 85% (w/w) solvent, about 15% (w/w) thickener. Additionally, between about 0.25% and 1% (w/w) of a fragrance may be added to the solution.

In an additional embodiment, 2-methylbut-2-enal may be incorporated into a solid carrier material to form a matrix composition containing the INTEROMONE® (or INTEROMONE® combined with at least one additional pheromone/INTEROMONE® or pheromone/INTEROMONE® composition), such as a fabric garment or a collar. The matrix containing the INTEROMONE® may be formed into a collar as is well known and amply described in the art, for example in U.S. Pat. No. 3,852,416. Typically an admixture of an active (i.e., an INTEROMONE®) and a carrier material providing the matrix is formed into strips through an extrusion process, and each strip is then formed a collar by including a fastening device such as a buckle, snap or hook. The solid carrier material forming the matrix into which the INTEROMONE® is incorporated is for example a polymer or polymer mixture with suitable release characteristics such that the pheromone is released from the collar to be inhaled by the animal. Additionally, the matrix containing the INTEROMONE® may be formed into a fabric garment as is described in the art, for example in U.S. Publication No. 2010/00319632. The INTEROMONE® preferably contributes from between about 0.001% and about 1% (w/w), and preferably between about 0.01% and 0.5% (w/w) of the collar or fabric garment.

Suitable polymers for forming a solid substrate for making a collar are well known and include, but are not limited to, polyethylene, polyvinyl acetate, ethylene acid copolymers, ethylene acrylates, polyurethanes, styrene-butadiene, polyvinyl butyral, polyvinyl chloride (PVC), polyolefin, polyacrylate, and polymethacrylate esters, and silicon polymer. The polymers can contribute between about 50% to about 99.99% (w/w) of the collar, and typically will contribute between about 90% and about 99.99% (w/w) of the collar. Plasticizers can be incorporated into the mixture to render the polymer resin more flexible. Suitable plasticizers include phosphoric acid esters (e.g. tricresyl phosphate) or phthalic acid esters (such as dioctyl phthalate or diisodecyl phthalate (DIDP)). The collar may also include other additives such as stabilizers, for example antioxidants to protect the collar material from degradation by UV light and other oxidizing factors. Lubricants, colorants, and fillers may also be included.

III Methods of Using an INTEROMONE® to Modify Behavior in an Animal

The present invention is further directed to a method of using INTEROMONE® to positively modify undesirable or inappropriate behaviors (e.g., barking, jumping, begging, and/or mobbing) or physiology in an animal by exposing the animal to an effective amount of an INTEROMONE®-based composition, wherein the composition comprises at least about 0.001% (w/w) of an INTEROMONE®. Generally, the composition comprises between about 0.001% and about 1% (w/w) of an INTEROMONE®. The animal can be exposed to the composition by any method allowing inhalation by the animal over a period of time sufficient to effect a modification of the target behavior, as determined according to behavioral observations. Typically, depending on the chosen route of administration, the particular animal, and situation, the exposure of the composition to the animal will be over a period of at least one second, but can also be for a period of at least one hour, for a period of between one hour and five hours, for a period of at least one day, for a period of at least one week, for a period of between one week and four weeks, for a period of at least one month, or for any period of time as may be needed to achieve a satisfactory behavioral effect. For example, an animal suffering from a temporarily induced anxiety (e.g., a trip to a veterinary office, being handled, or fireworks), may require a brief exposure to the composition before, during or after the anxiety-inducing event to relieve the anxiety and associated behavior. In contrast, an animal exposed to a stressful stimulus for a longer and continual period, such as a pet exposed to a new pet in the household, may benefit from regular exposure to the INTEROMONE® composition for an extended period.

Commonly recognized sources of stress in animals include for example weaning, transportation (especially in motorized vehicles), boredom, lack of exercise, separation anxiety, loud noises, events that induce barking/jumping/begging or anxiety, introduction to new people or animals, and visits to a veterinary office. Animals that are stressed by exposure to such events or conditions will typically exhibit highly undesirable stress-related behavioral symptoms. Such undesirable behaviors are commonly recognized and include for example fearful behavior such as cowering or shaking; excessive chewing, barking, begging, pacing, or excessive laying down; hyperactivity such as jumping; aggressive behavior toward people or other animals such as growling, snappishness or biting; property destruction; and frequent urination or soiling. The efficacy of the INTEROMONE® composition can be tested for example by spraying subject animals with an aerosol spray incorporating the composition, having the subject animals wear a collar incorporating the composition, or by applying the composition in the form of a liquid diffuser or the like in a physical area associated with the stress-inducing conditions for any given animal. In any case, the composition is sufficiently volatile for the animal to inhale and thus be exposed to a sufficient amount of the composition to produce a noticeable behavioral effect. For example, a reduction in undesirable outward behaviors is readily ascertainable (e.g. noticeable reduction in aggressive displays, barking and/or jumping) and can be supplemented by observing other physical indicators of stress such heart rate, weight changes, and secretion of stress hormones such as cortisol. When undesirable behaviors are observed, the composition of the present invention may be used to induce a temporary state of lower activity, calm and reduced excitability.

In use, the composition comprising an INTEROMONE® can be implemented in a number of different ways depending in part on the targeted animals and behavior desired to be modified. For example, an exemplary liquid spray formulation containing 2-methylbut-2-enal (dissolved in a suitable solvent) can be sprayed, for example, on the animal's nostrils, face, head or in its environment such that it may be perceived through olfaction as frequently as needed to obtain the desired behavioral modification. For example, an exemplary a liquid formulation containing 2-methylbut-2-enal can be delivered by way of a diffuser, such as a plug-in diffuser commercially available from as Central Life Sciences/Farnam Companies Inc. (Phoenix, Ariz.) as the Comfort Zone® Diffuser (sold with Feliway® or DAP® (Dog Appeasing Pheromone)). Alternatively, an INTEROMONE® in liquid, gas, or solid form can be incorporated in a plasticized material such as PVC or the like that can then be formed into a tag, or in strips to form a collar. Furthermore, the INTEROMONE® composition can be combined with at least one additional pheromone/INTEROMONE® or pheromone/INTEROMONE® composition (natural or synthetic) prior to implementation into any of the above-mentioned modes of delivery to the animal.

It should be understood that the INTEROMONE® used in the composition may be provided in the form of pure concentrate (100% concentration) or a diluted composition with additional excipients in the dosage form (i.e. the amount of active ingredient in the composition is less than or equal to 99.99%, and the remainder consists of inactive excipients). If diluted, the amount of INTEROMONE® dispensed in the various dosage forms may range from between about 1.0 pg/mL to about 1.0 g/mL, more preferably between about 1.0 ng/mL to about 1.0 g/mL. One of skill in the art will appreciate that the volume of active component added to the composition will need to be adjusted to account for the dilution and to ensure the end composition comprises the appropriate final concentration of INTEROMONE®. One of skill in the art will also appreciate that the various components of the composition may be provided in a variety of dosage forms including, but not limited to liquid solution or suspension, emulsion, aerosol, slow release matrices, and the like.

The compositions according to this invention may be applied in a variety of ways but are best applied by exposing the olfactory system by any means such as, for example, spraying a light mist directly on the facial region or in the environment of the animal whose behavior is intended to be modified. Further, the methods of the current invention are best accomplished by allowing the animal to inhale the composition, as the nasal cavities, sinuses, lungs and throats of animals present a large area for the aromatic molecules to be bound to an olfactory receptor. The application of the composition to the animal or the animal's environment may be repeated as often as necessary to modify the animal's behavior.

Unless otherwise defined, all technical and scientific terms used herein have the same meaning as is commonly understood by one of skill in the art to which this invention belongs at the time of filing. If specifically defined, then the definition provided herein takes precedent over any dictionary or extrinsic definition. Further, unless otherwise required by context, singular terms shall include pluralities, and plural terms shall include the singular. Herein, the use of "or" means "and/or" unless stated otherwise. All patents and publications referred to herein are incorporated by reference.

As used herein, "a" and "an" mean one or more, unless otherwise indicated.

As used herein, "INTEROMONE®", a registered trademark, means any naturally secreted or synthetically produced chemical released by one species, which, when administered to a member of a different vertebrate species, elicits a change in behavior or physiology of the different species with or without providing a benefit or harm to the species from which the chemical is released.

As used herein, "vertebrate" or "vertebrate species" is interchangeable with the word "animal" or "animal species" and encompasses any group of animals distinguished by possession of a vertebral column. Examples of vertebrate species include, but are not limited to, domestic animals such as cats and dogs; small animals, such as hamsters, rabbits, ferrets, rats, mice, and guinea pigs; commercial animals, such as horses, sheep, cattle, and swine; animals in captivity, such as apes, chimpanzees, tigers, lions, bears, elephants, zebras; amphibians such as frogs and salamanders; reptiles such as snakes, turtles, crocodiles, alligators, and lizards; birds, and the like.

Although the invention described herein is susceptible to various modifications and alternative iterations, specific embodiments thereof have been described in greater detail above. It should be understood, however, that the detailed description of the use of Androstenone is not intended to limit the invention to the specific embodiments disclosed. Rather, it should be understood that the invention is intended to cover all modifications, equivalents, and alternatives falling within the spirit and scope of the invention as defined by the claim language.

EXAMPLES

Example 1—Preparation of Spray Composition Comprising 2-methylbut-2-enal for Use on Dogs A pump spray formulation comprising 2-methylbut-2-enal was prepared in accordance with the formulation set forth in Table 1.

TABLE 1

| Pump Spray Composition Comprising 2-methylbut-2-enal as INTEROMONE ® | | |
|---|---|---|
| Ingredient | % | grams |
| 2-methylbut-2-enal | 0.01 | 0.01 |
| Isopropyl Alcohol | 10.00 | 10.00 |
| Lavender Chamomile fragrance #AA101592 | 0.50 | 0.5 |
| D.I. water | 89.49 | 89.49 |
| Total | 100.00% | 100 |

Example 2—Determining the Efficacy of a Spray Composition Comprising an INTEROMONE® in Modifying Behavior of Dogs A spray composition comprising 2-methylbut-2-enal as an Interomone® was prepared in accordance with Example 1.

Four dogs were fitted with cloth jackets that contained electrodes to measure their heart rate. One dog was sprayed with the 2-methylbut-2-enal composition, one dog was sprayed with a placebo, and two dogs were sprayed with pheromone-based products currently on the market for purposes of modifying behavior. The dogs in each group were sprayed in the face to ensure the dog had an olfactory experience with the liquid formulations. Data were collected for two hours following application of the spray to the facial/snout region of the four dogs. The control period was indicated as time zero ("0") on FIG. 1 and FIG. 2.

Figure 2:
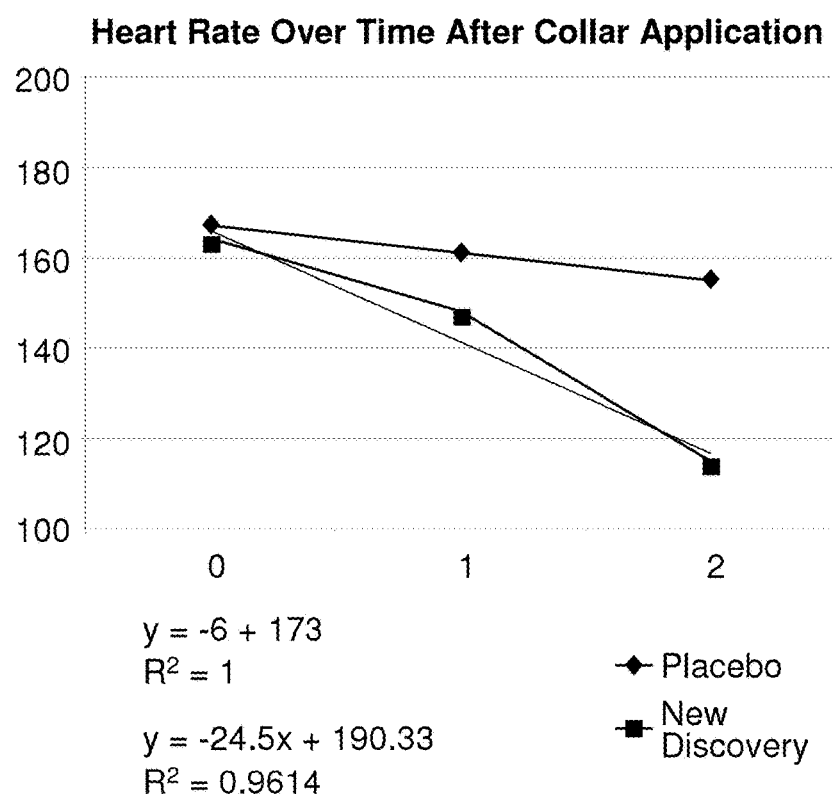
FIG. 2 is a graphic representation of a comparative test of dogs receiving a placebo and a composition comprising 2-methylbut-2-enal (New Discovery).

As shown in FIG. 1, the spray containing the 2-methylbut-2-enal was found to reduce the average dog heart rate 24.5 beats/min per hour and reduced heart rate by 30% over the two hour period when compared to the products currently on the market and the placebo. FIG. 2 compares the effect of the spray containing the 2-methylbut-2-enal with the placebo to emphasize the greater reduction in heart rate when the dogs were exposed to the INTEROMONE® product of the present disclosure over the two-hour period.

Example 3—Preparation of a PVC Collar Containing 2-Methylbut-2-Enal as INTEROMONE® for Use on Dogs A collar containing 2-methylbut-2-enal can be prepared according to typical industry techniques as described hereinabove. Table 2 is the list of ingredients that can be used to prepare a collar comprising a rabbit pheromone.

TABLE 2

Collar Comprising 2-methylbut-2-enal as INTEROMONE ®

| Ingredient | % | grams |
| --- | --- | --- |
| 2-methylbut-2-enal | 0.02 | 0.02 |
| MU-760000 (Microthene) | 99.780 | 99.780 |
| Corona magenta - Pink (DayGlo) | 0.100 | 0.100 |
| Blue #2 (DayGlo) | 0.100 | 0.100 |
| Total | 100.00% | 100 |

Example 4—Preparation of a PVC Collar Containing 2-methylbut-2-enal and an Additional Pheromone for Use on Dogs A collar containing 2-methylbut-2-enal and an additional pheromone composition can be prepared according to typical industry techniques as described hereinabove. Table 3 is the list of ingredients that can be used to prepare a collar comprising a rabbit pheromone and an additional pheromone composition.

TABLE 3

Collar Comprising 2-methylbut-2-enal as INTEROMONE ® and an Additional Pheromone

| Ingredient | % | grams |
| --- | --- | --- |
| 2-methylbut-2-enal | 0.02 | 0.02 |
| MU-760000 (Microthene) | 93.88 | 93.88 |
| Pheromone H (ModernVeterinary Therapeutics, Florida) | 6.00 | 6.00 |
| Blue #2 (DayGlo) | 0.100 | 0.100 |
| Total | 100.00% | 100 |

Example 5—Preparation of a Room Diffuser Containing 2-methylbut-2-enal and Use on Dogs A room diffuser formulation containing 2-methylbut-2-enal can be prepared according to typical industry techniques described above. Table 4 is the list of ingredients that can be used to prepare a diffuser formulation comprising a rabbit pheromone.

TABLE 4

Diffuser Formulation Comprising 2-methylbut-2-enal as INTEROMONE ®

| Ingredient | % | grams |
| --- | --- | --- |
| 2-methylbut-2-enal | 0.02 | 0.02 |
| Isopropyl Palmitate | 15.00 | 15.00 |
| Lavender Chamomile frag. #AA101592 | 0.5 | 0.5 |
| QC-9180 Silicone Fluid 0.65 CS | 84.48 | 84.48 |
| Total | 100.00% | 100 |

Example 6—Determining the Efficacy of 2-methylbut-2-enal as an INTEROMONE® in Adult Dogs when Administered in Liquid (Spray and Room Diffuser) Form Four distinct studies were conducted for purposes of examining and determining the efficacy of 2-methylbut-2-enal, a rabbit maternal pheromone, as an INTEROMONE® in dogs when administered in liquid form (e.g., spray and room diffuser).

Eight dogs were obtained from a local contract research facility and assessment was made as to general dog health, behavior and heart rate. The dogs were estimated to be 2 to 7 years of age, mixed breed, and weighed averagely 8.1±0.18 kg at the start of the studies. The average body weight and feed intake of the dogs did not significantly change over the course of the studies. Upon arrival each dog was bathed using shampoo containing flea and tick medicine (Hartz Mountain Corp. Secaucus, N.J. USA), and their body hair was shaved. Each dog was kept in a single room, which had 100% fresh air intake and exhaust. The dogs were fed twice (am and pm) per day ad libitum. At that time, the room was cleaned and the dogs obtained extra exercise. Water was available ad libitum.

Dog sex, behavior, and average heart rate are provided in Table 5. As shown in Table 5, all eight dogs were generally nervous types and varied in other behaviors such as shy, aggressive or pacing.

TABLE 5

Dog Sex and Behavioral Types.

| Dog number | Sex | Avg Heart Rate* | Behavioral Type |
| --- | --- | --- | --- |
| 1 | Male | 204.9 | Nervous |
| 2 | Male | 117.0 | Nervous, aggressive, biting |
| 3 | Male | 140.0 | Nervous, pacing |
| 4 | Male | 137.9 | Nervous, shy |
| 5 | Male | 140.6 | Nervous, pacing |
| 6 | Female | 78.4 | Nervous, inactive |
| 7 | Male | 81.8 | Nervous, runs away from people |
| 8 | Female | 65.4 | Nervous, head down, avoids people, difficult to catch |

*SE pooled = 10.7 bpm. Dogs 1-4 were present at one period while dogs 5-8 were present about 8 weeks later. Among dogs used in the collar/spray study, dog 1 had elevated basal HR. Among dogs used in the room diffuser study, dog 5 had elevated HR compared to the other three dogs (6-8).

Dog behavior was captured on video media at a sampling rate of 30 frames per second. Video records were reviewed in real time (with tape playing 30 frames per second). A scan sampling method was used to record dog behaviors each minute or each 5 minutes depending on the particular study.

If the sample period was 120 minutes with four periods (0-30=0, 30-60=30, 60-90=60, and 90-120-90 min), then a scan sample was recorded each 1 minute. If the sample period was 24 hours, then the scan sample was collected each 5 minutes and summarized each hour. A list of observed dog behaviors and their definitions are provided in Table 6. For example, pacing is when a dog walks in a stereotyped manner for minutes to hours. Because it was not easy to distinguish walking from pacing, the behaviors were merged. In addition, the video records could not clearly distinguish lying down and awake versus lying down and sleeping, therefore there was no separate description for these two behaviors.

TABLE 6

Definitions of Behaviors Used in This Study

| Behavior | Definition |
| --- | --- |
| Pace-walk | Locomotion in any pattern |
| Stand | Supported by limbs, not moving/walking/pacing |
| Sit | Posterior on ground while front feet support the animal |
| Lying down | Dog's body not supported by any limb. |
| Lick self | Tongue touching any self body part |
| Eat | Head in dog bowl |
| Drink | Head in water bowl |
| Urinate | Urine stream observed |
| Defecate | Defecation observed |
| Activity | Obtained by calculation; all behaviors other than lying down; also, the inverse of lying down. |

Heart rate during the studies was measured by the use of a non-invasive telemetry system (Data Science International, St. Paul, Minn., USA). Leads were placed in contact with the dogs' shaved skin. Sensors measured heart rate, surface temperature and general activity. Data were transmitted to a receiving computer in another room. The sampling rate varied with the study, but was 5 seconds for the first two hours after treatments and then each 1 minute for 24 hours (depending on the particular study). For surface temperature measurements of the dog subjects, a thermistor was located against the skin of each dog. It recorded the surface temperature to the neared 0.1° C. on the same interval as the heart rate data.

Behavior and physiological data (heart rate and surface temperature) were analyzed by least squares analysis of variance using SAS (2011) software and the general linear models procedures. The experimental design of each study was a specialized randomized complete block in a Latin square design with data collected as a split plot over time. Dogs represented the blocks. Each dog received each treatment randomly in successive days or weeks. The statistical model included effects of treatment (TRT), dog, dog by treatment (TRT*DOG; error term used to assess treatment and dog effects), time (HR), treatment by time (TRT*HR), and residual error (SE; used to test remaining effects). Behavior data were collected and analyzed as counts per time period, but for clarity of presentation, the data are reported as percentage of time dogs engaged in each behavior.

Studies and Results

Study 1

In Study 1, baseline heart rate data were collected while the dogs each experienced 4 different treatments—a placebo collar (PLACEBO), Pheromone "H" Collar (SERG), Dog Appeasing Pheromone in collar form (DAPC) and the Rabbit Pheromone (RP; 1 µg/mL) formulated into a spray in accordance with Example 1. Each of the four treatments was given to each dog in a random order, with the treatment changing each week. Baseline heart rate and behavior data were collected for 30 minutes before each treatment application (see Table 7) and 2 hours after (see Table 8) (expressed in % of time).

TABLE 7

Difference Among Dogs in Baseline Behavior

| Dog | PW | Stand | Sit | Lying | Lick self | Eat | Drink | Defecate | Urinate |
| --- | --- | --- | --- | --- | --- | --- | --- | --- | --- |
| 1 | 0.0% | 2.8% | 55.0% | 76.7% | 0.0% | 0.0% | 0.0% | 0.0% | 0.0% |
| 2 | 0.0% | 0.0% | 35.8% | 85.6% | 0.0% | 0.0% | 0.0% | 0.0% | 0.0% |
| 3 | 36.1% | 0.0% | 58.3% | 58.9% | 0.0% | 8.3% | 0.0% | 0.0% | 0.0% |
| 4 | 0.0% | 0.0% | 13.9% | 94.4% | 0.0% | 0.0% | 0.0% | 0.0% | 0.0% |
| 5 | 19.4% | 13.9% | 83.3% | 52.2% | 0.0% | 0.0% | 2.8% | 0.0% | 0.0% |
| 6 | 0.0% | 0.0% | 0.0% | 100M | 0.0% | 0.0% | 0.0% | 0.0% | 0.0% |
| 7 | 50.0% | 0.0% | 25.0% | 60.0% | 0.0% | 25.0 | 0.0% | 0.0% | 0.0% |
| 8 | 0.0% | 0.0% | 0.0% | 100.0% | 0.0% | 0.0% | 0.0% | 0.0% | 0.0% |
| SE | 11.5% | 2.9% | 29.7% | 14.3% | 0.0% | 6.1% | 1.0% | 0.0% | 0.0% |
| P-value | 0.06 | 0.04 | 0.46 | 0.17 | . | 0.22 | 0.51 | . | . |

TABLE 8

Baseline Dog Behaviors (% of time) During 120 minutes After Treatment

| Behavior | PLACEBO | SERG | DAPC | RP | SE | TRT | TRT*DOG | TRT*HR |
| --- | --- | --- | --- | --- | --- | --- | --- | --- |
| Pace-walk | 13.4 | 12.2 | 24.3 | 7.6 | 10.4 | 0.71 | 0.0037 | 0.18 |
| Standing | 2.2 | 9.0 | 12.5 | 3.1 | 3.4 | 0.14 | 0.052 | 0.17 |

TABLE 8-continued

Baseline Dog Behaviors (% of time) During 120 minutes After Treatment

| Behavior | PLACEBO | SERG | DAPC | RP | SE | TRT | TRT*DOG | TRT*HR |
|---|---|---|---|---|---|---|---|---|
| Sitting | 33.6 | 47.6 | 68.1 | 93.1 | 22.4 | 0.29 | 0.001 | 0.016 |
| Lying down | 78.6 | 71.9 | 58.0 | 58.5 | 10.0 | 0.40 | 0.001 | 0.52 |
| Lick self | 0 | 0 | 0 | 0 | 0 | — | — | — |
| Eat | 4.1 | 1.4 | 0.0 | 0.0 | 1.6 | 0.25 | 0.079 | 0.090 |
| Drink | 0.3 | 0.0 | 0.0 | 0.0 | 0.2 | 0.50 | 0.48 | 0.42 |
| Defecate | 0 | 0 | 0 | 0 | 0 | — | — | — |
| Urinate | 0 | 0 | 0 | 0 | 0 | — | — | — |

DAPC = Dog Appeasing Pheromone in collar form; RP = Rabbit pheromone, SERG = Sergeant's pheromone collar; TRT = Pheromone/INTEROMONE ®treatment; HR = hour or time; SE = residual error.

Results as to Behavior:

The overall treatment effects were not statistically significant (see Table 8), however a large number of treatment by dog (TRT*DOG) effects and one treatment by hour (TRT*HR) effect were identified as indicated in Table 8. Some dogs responded to some treatments differently.

The statistically-significant interactions set forth in Table 8 (pace-walk, lying down, and sitting) are represented in FIGS. 3A, 3B, 3C, and 3D. FIG. 3A illustrates pacing-walking behavior following the different treatments. Some dogs did not pace. Dogs 4, 6, and 8 showed little or no pacing. Dog 1 showed increased pacing-walking when it experienced the DAP collar (DAPC); Dog 3 showed increased pacing-walking when it experienced the SERG collar in comparison to DAP collar or RP spray; and that, relative to the Placebo collar, dog 7 showed reduced pacing-walking compared with the DAP collar or RP spray.

Lying down behavior was also compared to the dogs' general activity. Dogs 3, 4, 5, 6, and 7 were not significantly influenced by treatments. However, the significant dog treatment interaction (P<0.001) was explained by differential effects on treatments among dogs 1, 2, and 8 as illustrated in FIG. 3B. Compared with the Placebo treatment, dog 1 had reduced lying down with the DAP collar, meaning that the DAP collar increased this dog's activity. For dog 2, both SERG and RP reduced lying down behavior significantly and increased the dog's activity. For dog 8, only RP increased dog activity and reduced lying down compared with the placebo treatment.

Sitting behavior is represented in FIG. 3C for the four dogs in which sitting differed between treatments and the placebo (dogs 2, 3, 7 and 8). SERG collar increased sitting only in dog 2. RP spray increased dog sitting in dogs 2 and 8 compared to the Placebo. The DAP collar increased sitting behavior in dogs 3, 7 and 8. Dog sitting behavior was further influenced by the effects of treatment over time (i.e., the 2-hour period after collar or spray application) as shown in FIG. 3D. When dogs experienced the Placebo, they sat down less over time (from nearly 30% of their time to 10% or less). In contrast, in the 30 minute period after rabbit pheromone spray, dogs sat an average of nearly 50% of the time. In the 60 minute period after treatment with rabbit pheromone, dogs also sat more than with the other treatments, including the Placebo. At the 90 minute period after DAP collar application, dogs sat more than dogs given the placebo collar. These results demonstrated that the rabbit pheromone spray calms dogs faster than treatment with DAP collar.

Figure 4:
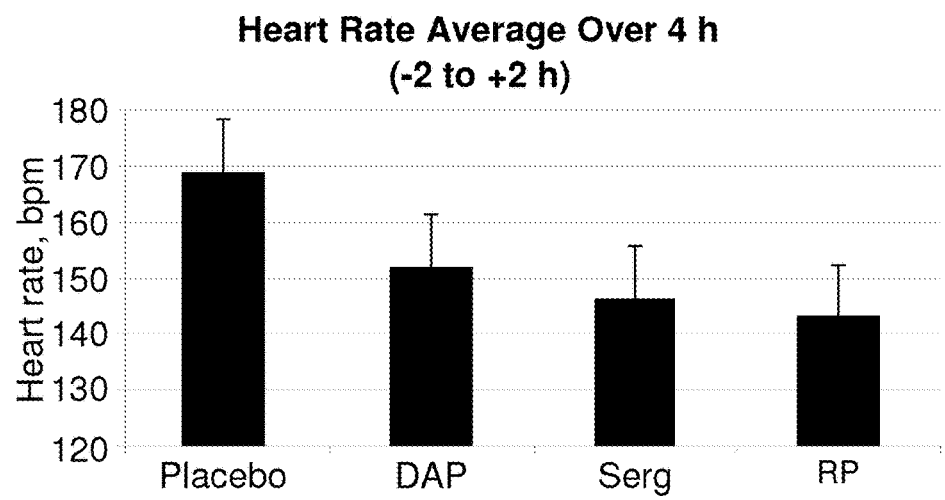
FIG. 4 is a graphic representation of the average heart rate of dogs 1-4 over the periods from 2 hours before collars or sprays to 2 hours after collars or sprays.
Figure 5:
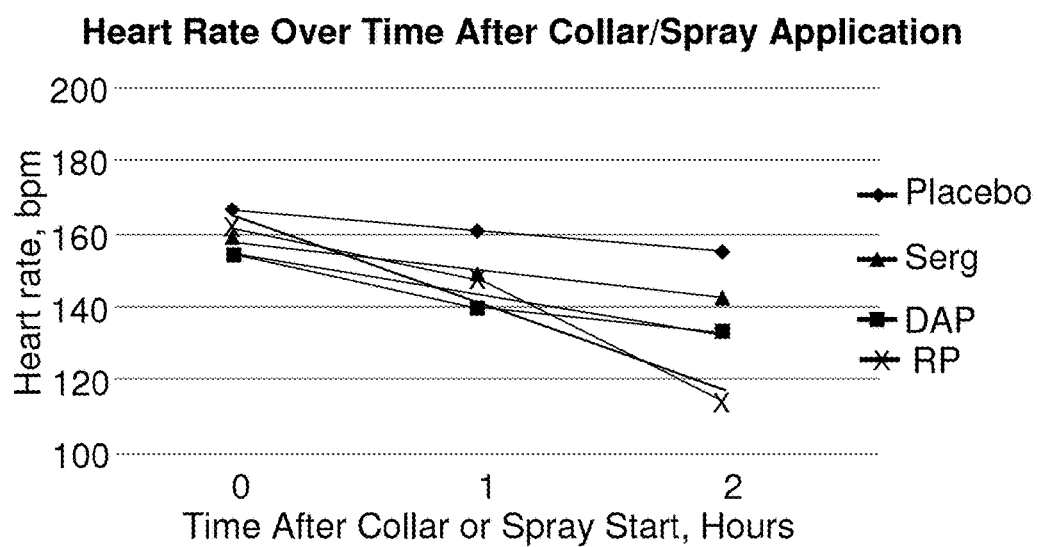
FIG. 5 is a graphic representation of effects of collar or spray of pheromone/INTEROMONE® on heart rate of dogs 1-4.
Figure 6:
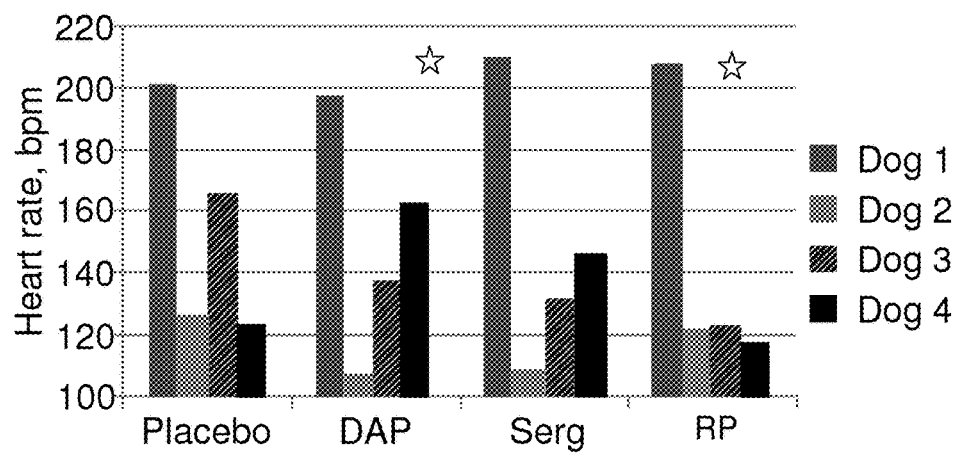
FIG. 6 is a graphic representation of differential dog response to the pheromone treatments (Placebo, DAP, Serg, and RP).

Results as to Heart Rate:

Using data collected through the entire study period, all three treatments were found to generally decrease overall dog heart rate (HR) in dogs 1-4 as shown in FIGS. 4, 5, and 6. However, the rabbit pheromone treatment most significantly (P<0.05) reduced overall dog heart rate (see FIGS. 4 and 5). Dog heart rates did not differ when first exposed to any odor; however, the dogs experiencing rabbit pheromone by spray had a greater decline in heart rate than Placebo (see FIG. 5). All treatments resulted in a significant (P<0.05) decrease in heart rate over the two hour period after collar application. However, the dogs experiencing rabbit pheromone by spray had a greater decline in heart rate than the Placebo in the first two hours after pheromone application (see FIG. 5).

The regression equations for each line are given in the legend to FIG. 5. The slopes of the equations represent the speed of the heart rate decline under each treatment. Placebo-treated dogs had a heart rate decline of 6 bpm/h, while the decline in heart rate for the SERG collar was 8.5 bpm/h. The DAP collar-treated dogs declined in heart rate by 10 bpm/h. Dogs treated with rabbit pheromone reduced their heart rate by 24.5 bpm/h. Therefore, RP had the greatest effect in decreasing dog heart rate (FIG. 5). The observation of this decline rate difference is consistent with the observation of the overall findings presented in FIG. 4 that heart rate average under RP was significantly lower than Placebo treatment.

As shown in FIG. 6, dog 1 had elevated basal heart rate and was not influenced by any of the treatments. All treatments generally lowered the heart rate of dog 2, but not significantly. Dog 3 had decreased heart rate with the rabbit pheromone spray when compared to the Placebo collar. Dog 4 had increased heart rate with the DAP collar. Therefore, with the exception of dogs 1 and 2, which were not significantly affected by any treatments, RP decreased the heart rates of dogs 3 and 4 compared to other treatments.

Integrating Behavior and Heart Rate in Study 1

Figure 3:
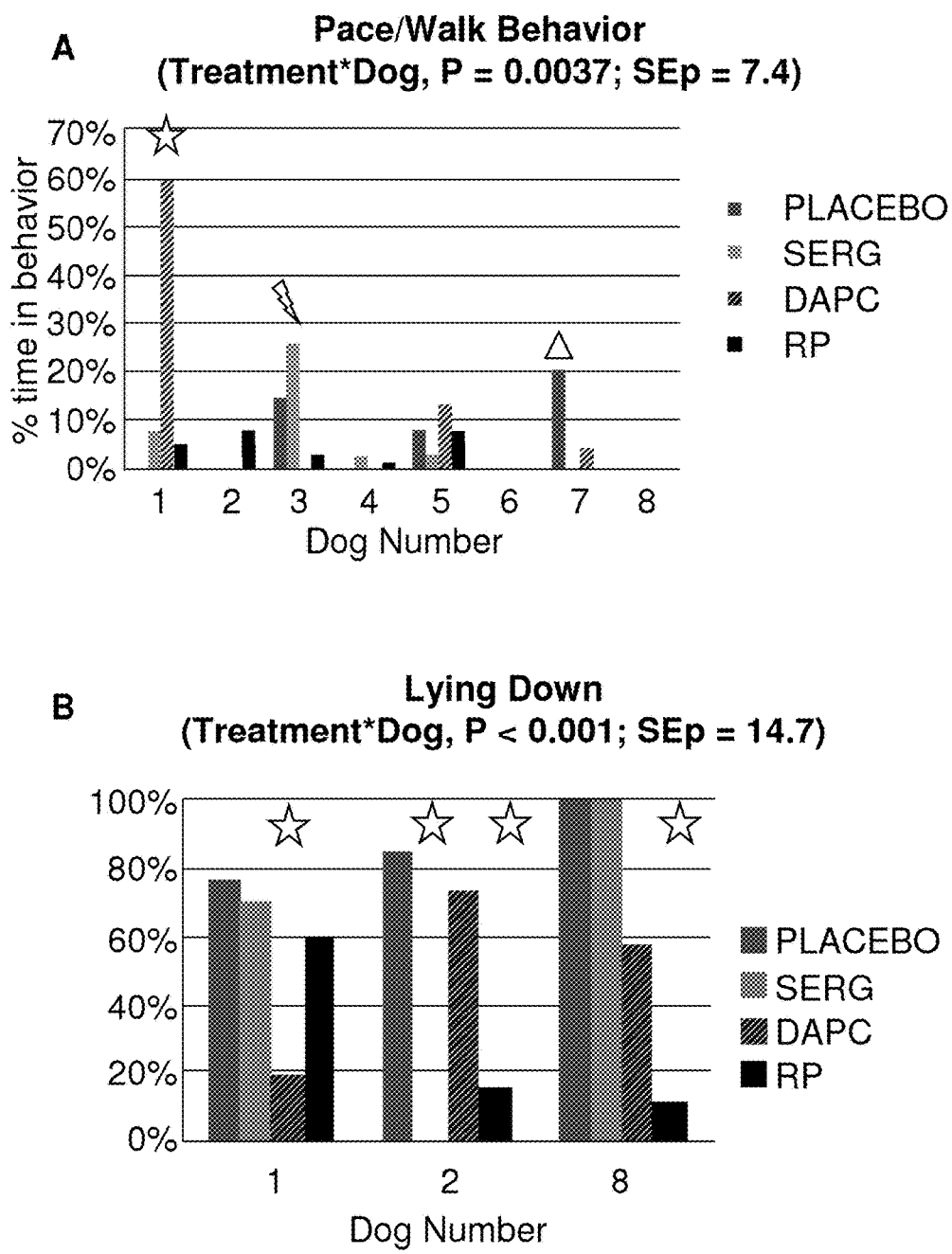
FIG. 3 graphically depicts statistically-significant ($P<0.05$) interactions observed in study 1 of Example 6. These interactions include the dog pace/walk behavior (FIG. 3A), the lying down behavior (FIG. 3B), and the sitting behavior (FIG. 3C).

The behavior and HR data were integrated in order to extrapolate further information. Dog 1 had a very high heart rate; dogs 3, 4 and 5 had intermediate elevated heart rate; and dogs 2, 6, 7, and 8 had approximately normal heart rate (around 80-120 bpm). FIG. 3 shows that dogs 3, 5 and 7 were more active overall. Most of the increased behavioral activity of these three dogs was in pacing-walking. Dog 5 stood or sat when it was not pacing-walking and it showed the least amount of lying down; dog 7 showed the most pacing-walking and it sat at a moderate rate. In a sharp contrast, dogs 6 and 8 spent 100% of their time during the Placebo treatment lying down (inactive). Only sporadic eating and drinking were observed in these two dogs during baseline/Placebo observations and no defecation or urination was observed.

Figure 7:
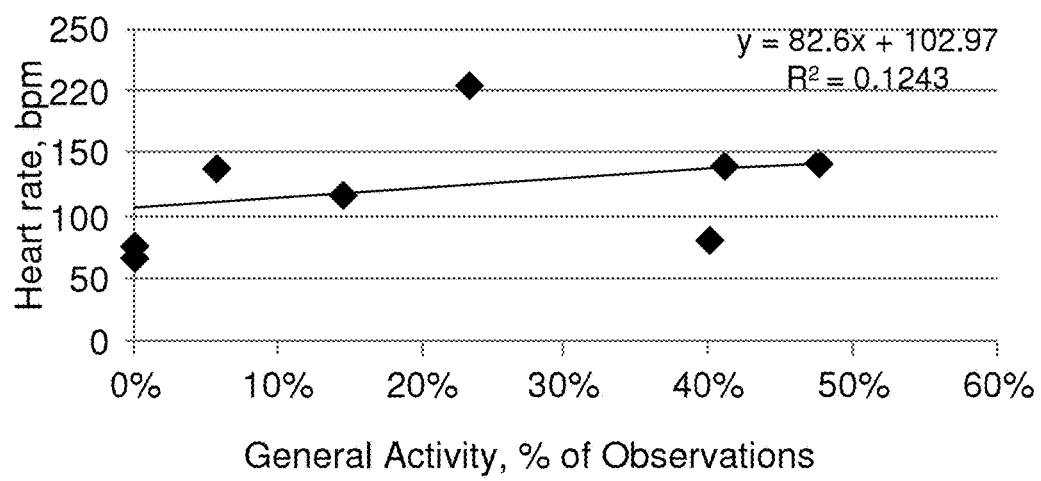
FIG. 7 is a graphic representation of the relationship between dog heart rates and general activity.

The correlation coefficient between HR and general activity was 0.34 (FIG. 7), which is a moderate to weak correlation. This finding suggested that dog heart rate was higher or lower based on more than just dog activity (e.g., pacing-walking) and confirms that some dogs had naturally elevated heart rates for reasons other than their natural behaviors. In addition, of the dogs that paced-walked a large amount of time (dogs 3, 5 and 7), dogs 3 and 5 had elevated heart rate, but dog 7 did not have an elevated heart rate. Dog 3 had moderately elevated heart rate during baseline/Placebo exposure. Rabbit pheromone decreased heart rate in dog 3, which was expressed by pacing-walking less (FIG. 3A).

Overall, all the collars and the spray reduced heart rate over time. This reduced heart rate was accompanied by increased sitting (FIG. 3C) in some dogs. Compared with Placebo, dogs 2 and 8 showed increased sitting in response to the rabbit pheromone.

Study 2

In Study 2, the dogs were exposed to the same treatments as in Study 1, except a startle was also applied. An aerosol can (Pet Corrector, The Company of Animals, Surrey, UK) was used to make a loud hissing noise and a spray of liquid as a startle. The protocol involved spraying the Rabbit Pheromone at 0, 30, 60, and 90 min (RP; 1 µg/mL) or collar application (PLACEBO, SERG, or DAPC) at time zero. Each dog was startled at 45 minutes. Data were recorded for 120 minutes. Data reporting periods were: 0 (0-30 min), 30 (30-60 min), and 90 (90-120 min).

Results as to Behavior:

The overall dog behavior after being startled once every 30 minutes for a period of 120 minutes are given in Table 9. The treatment by dog interaction was significant (P<0.01) for sitting and lying down behaviors. As shown in Table 9, startling the dogs increased standing behavior among RP-sprayed dogs in comparison to the dogs experiencing the Placebo or SERG collars.

each dog and not all dogs responded the same to each pheromone/INTEROMONE®.

Figure 10:
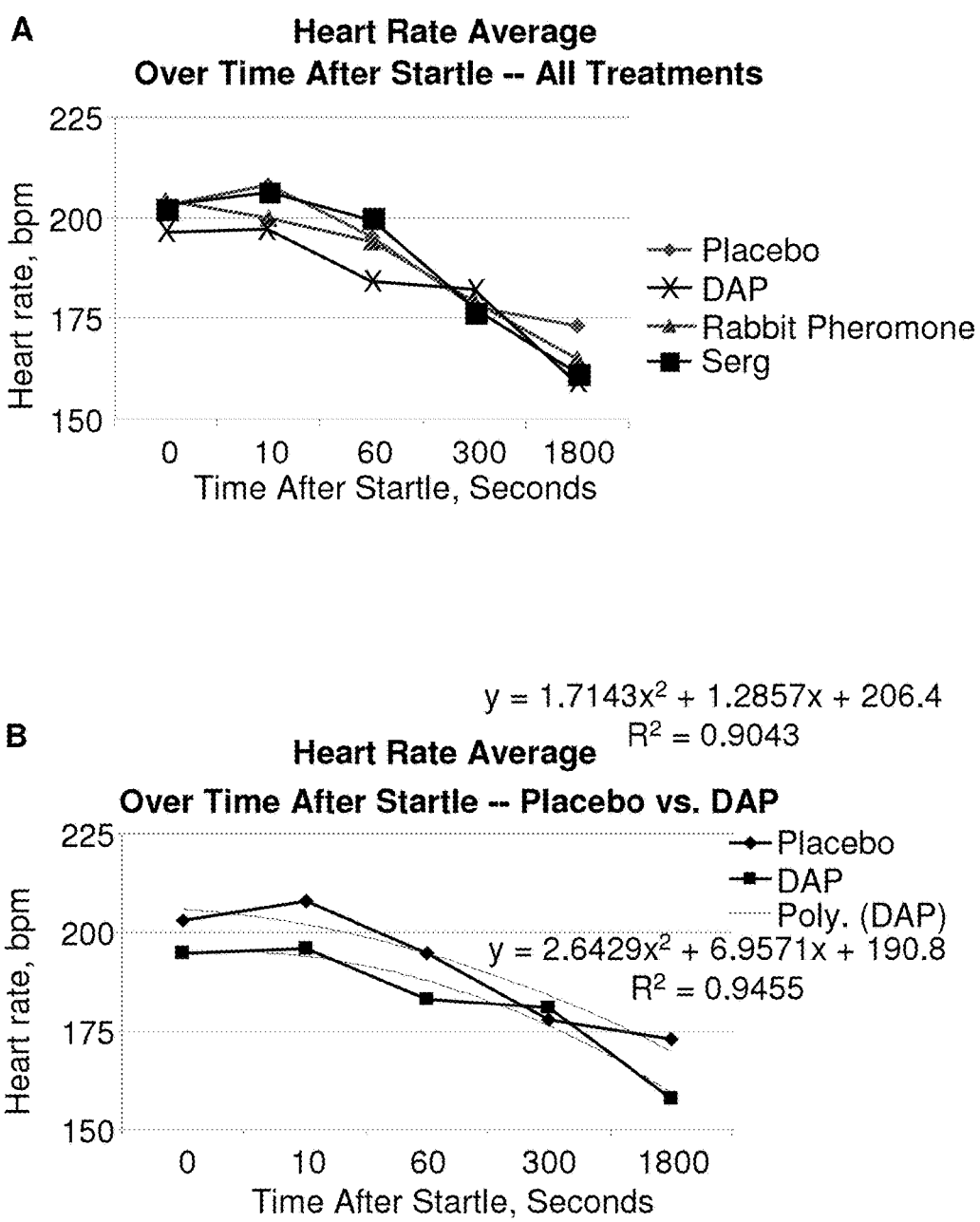
FIG. 10 is a graphic representation of effects of four treatments on dog heart rates over 30 min (1,800 s) after startle.
Figure 10:
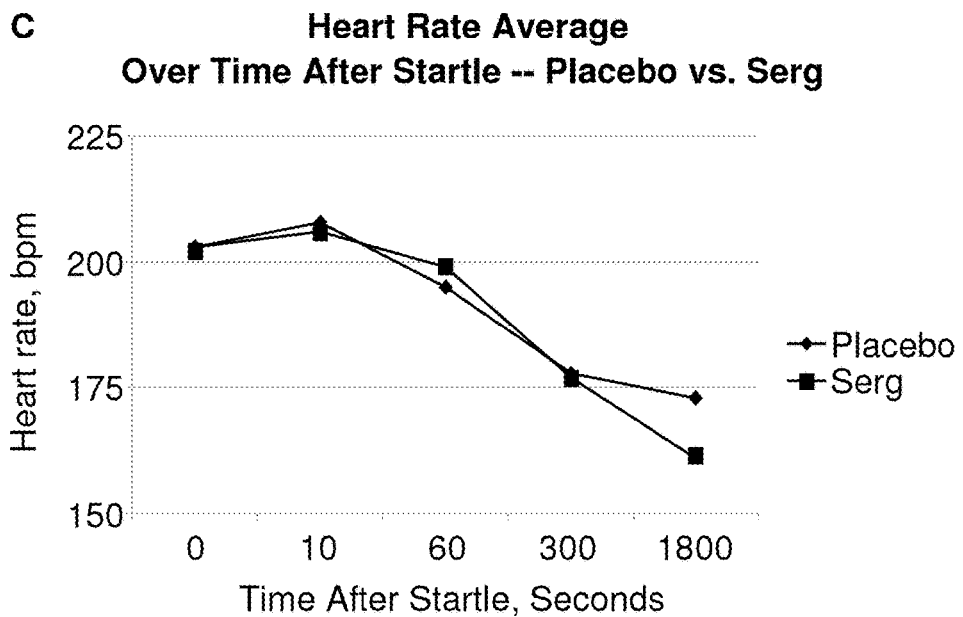
Figure 10:
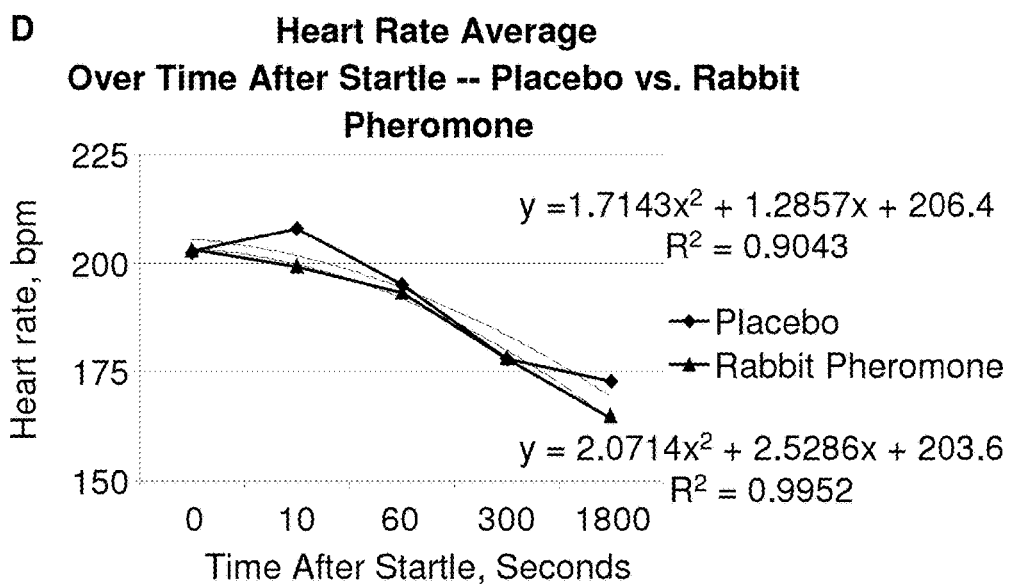

Results as to Heart Rate:

Dog heart rates in bpm (beats per minute) are shown in FIG. 10 in relation to treatments. After startle, all dog heart rates rose for about 10 seconds, then decreased (FIG. 10A) over a 30-minute period. Each treatment had a similar decline in heart rate over time; regression lines/equations for the Placebo and each treatment (FIG. 10B-D) are given and show a similar slope over time for each treatment. None of the pheromones/INTEROMONE® caused a different decline change over time or mean compared with the Placebo treatment group.

Integrating Behavior and Heart Rate in Study 2:

Because dog heart rates increased less than 5% after the startle (note the first 10 seconds in FIG. 10), the startle was not very severe. However, in this moderate startle model, individual dogs responded in one of three ways: no change, increase lying down or increase in sitting behavior. These behavioral responses represent a decrease in behavioral activity with concomitant decline in heart rates over time. Although each pheromone/INTEROMONE® ended with an apparent mean heart rate lower than the Placebo (at time 90 min), the treatment means did not differ significantly from the level of the Placebo treatment group. Thus, these pheromones/INTEROMONE® compositions did not improve the heart rates of startled dogs.

Study 3

In Study 1 and 2, the DAP was applied as a collar and the rabbit pheromone as a spray. To test if the physical form of the pheromone/INTEROMONE® impacted its efficacy, Study 3 examined the behavior and heart rate effects of Dog

TABLE 9

Dog Behaviors During the 120 minutes After Startle (% of time)

| Behavior | PLACEBO | SERG | DAPC | RP | SE | TRT | TRT*DOG | TRT*HR |
|---|---|---|---|---|---|---|---|---|
| Pace-walk | 10.8 | 6.6 | 12.8 | 19.4 | 5.8 | 0.49 | 0.40 | 0.53 |
| Standing | 4.9a | 3.8a | 8.7$^{a, b}$ | 23.4$^b$ | 5.3 | 0.06 | 0.14 | 0.14 |
| Sitting | 22.6 | 41.7 | 32.6 | 53.8 | 17.8 | 0.66 | 0.001 | 0.07 |
| Lying down | 61.0 | 54.6 | 55.8 | 46.4 | 7.6 | 0.20 | 0.0006 | 0.08 |
| Lick self | 1.0a | 0.0b | 0.0$^b$ | 0.0$^b$ | 0.5 | 0.41 | 0.50 | 0.45 |
| Eat | 0.7 | 0.0 | 0.0 | 1.2 | 0.6 | 0.51 | 0.44 | 0.57 |
| Drink | 0.7 | 0.0 | 0.0 | 3.7 | 1.6 | 0.36 | 0.06 | 0.68 |
| Defecate | 0.3 | 0.0 | 0.3 | 0.0 | 0.3 | 0.61 | 0.45 | 0.70 |
| Urinate | 0.0 | 0.3 | 0.7 | 0.0 | 0.3 | 0.32 | 0.43 | 0.27 |

Abbreviations: DAPC = Dog Appeasing Pheromone in collar form; Placebo = collar with Sergeant's Formula H; RP = Rabbit pheromone, SERG = Sergeant's collar; TRT = Pheromone/INTEROMONE® treatment; HR = hour or time.

Figure 8:
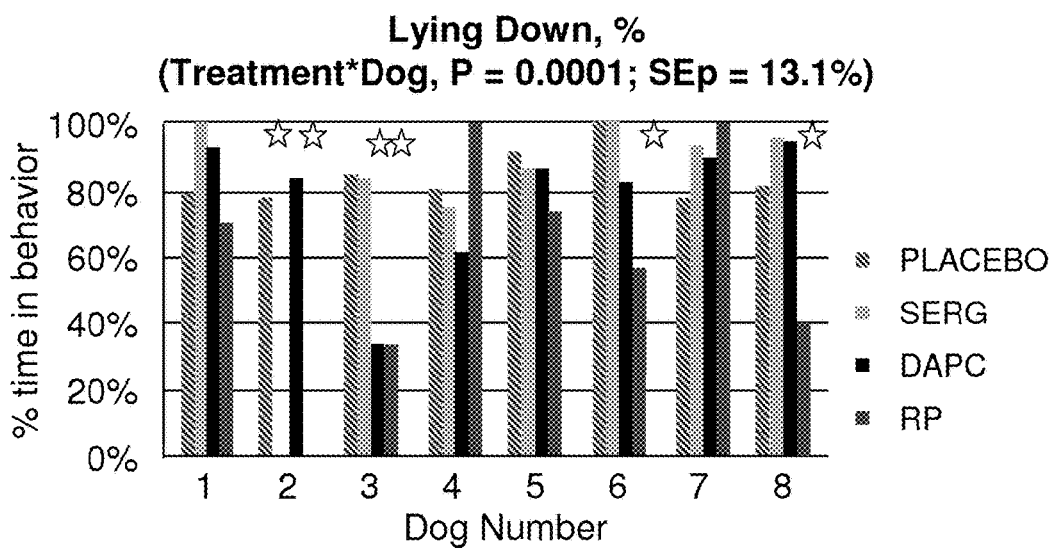
FIG. 8 is a graphic representation of lying down behavior for eight dogs each given one of four treatments and startled.
Figure 9:
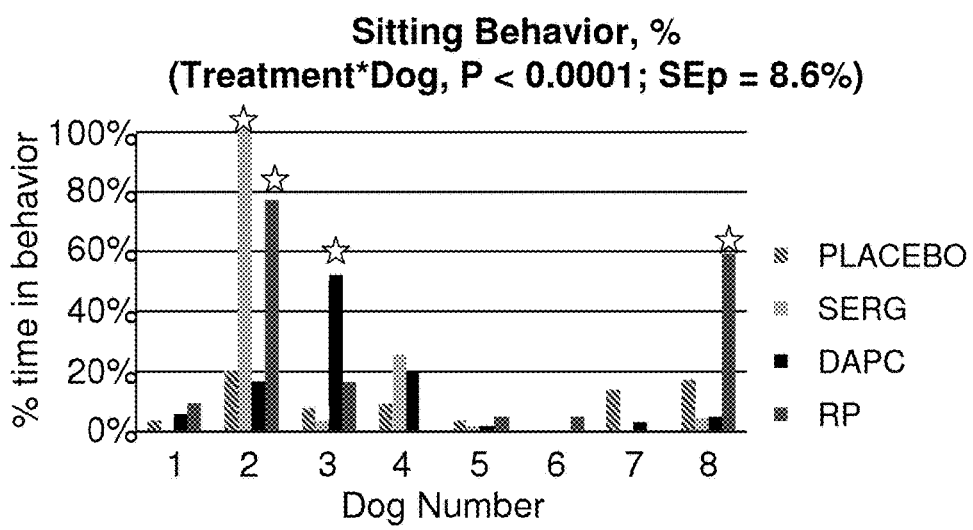
FIG. 9 is a graphic representation of sitting behavior for eight dogs each given one of four treatments and startled.

The individual dog lying down behavior is shown in FIG. 8 and individual dog sitting behavior is shown in FIG. 9. Most dogs lay down after being startled; however, some dogs became more active by sitting more and lying down less after startle. For example, dogs 2, 3, 6 and 8 spent less time lying down but more time sitting after startle when RP was sprayed (FIG. 9). Dog 3 also showed less lying down and more sitting when DAP collar was used. Dog 2 was more active (less time lying down) and increased sitting after startle when it experienced the Serg collar (FIGS. 8 and 9). Therefore, the most common outcome for more than half of the dogs was to increase activity by sitting more and lying down less after certain pheromones/INTEROMONE®. Not all pheromones/INTEROMONE® had the same effects on Appeasing Pheromone (DAP) and rabbit pheromone (RP) both applied as a spray after startle in order to obtain a direct comparison between sprays. Accordingly, Study 3 examined the relative effect of DAP spray (DAPS) and RP spray on the behavior and heart rate of the dog subjects. Both treatments were given to each dog in a random order. In this study, the Behavior data were collected from dogs 1-8 while heart rate data were collected from dogs 1-4.

Results as to Behavior:

Some main effects of treatments were observed and are presented in Table 10. Dogs given the RP spray tended to sit more (P=0.068) than DAP sprayed dogs. In addition, dogs sprayed with DAP both drank and urinated more (P<0.03) than dogs sprayed with rabbit pheromone.

TABLE 10

Dog Behavior under DAPS or RP Spray with Startle (% of time)

| Behavior | DAP | RP | SE | TRT | TRT*DOG | TRT*HR |
|---|---|---|---|---|---|---|
| Pace-walk | 6.7 | 9.8 | 13.3 | 0.63 | 0.001 | 0.96 |
| Standing | 6.0 | 3.7 | 8.55 | 0.53 | 0.032 | 0.58 |
| Sitting | 15.7 | 35.4 | 5.87 | 0.068 | 0.10 | 0.12 |
| Lying down | 49.8 | 43.8 | 39.03 | 0.32 | 0.0007 | 0.80 |
| Lick self | 0.42 | 0 | 0.037 | 0.68 | 0.630 | 0.44 |
| Eat | 0 | 0 | — | — | — | — |
| Drink | 0.17 | 0 | 0.04 | 0.037 | 0.99 | 0.23 |
| Defecate | 0 | 0.93 | 2.51 | 0.17 | 0.0007 | 0.38 |
| Urinate | 0.17 | 0 | 0.04 | 0.037 | 0.997 | 0.23 |

Figure 11:
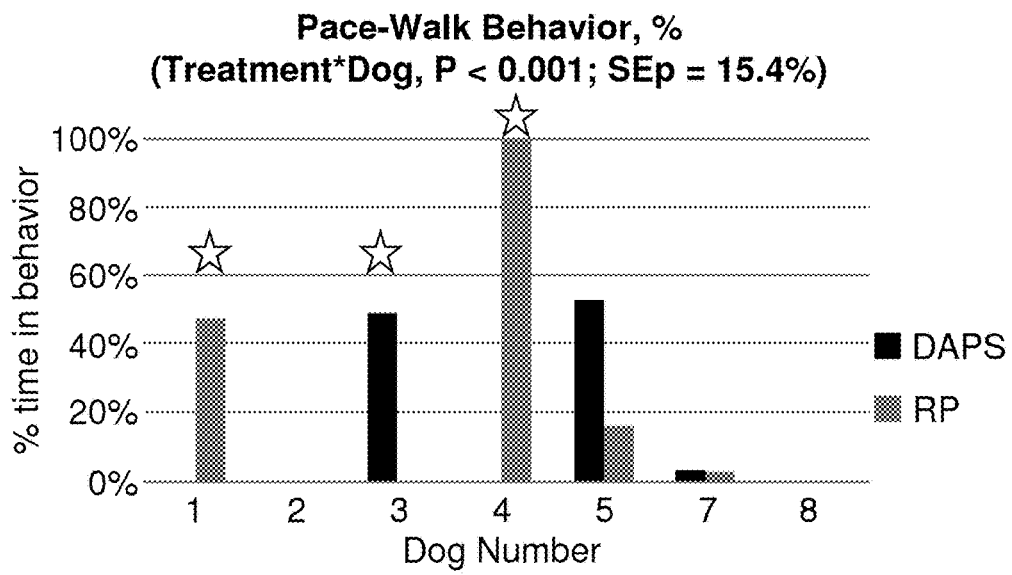
FIG. 11 is a graphic representation of effects of DAPS and RP in spray form on dog pacing-walking behaviors.
Figure 12:
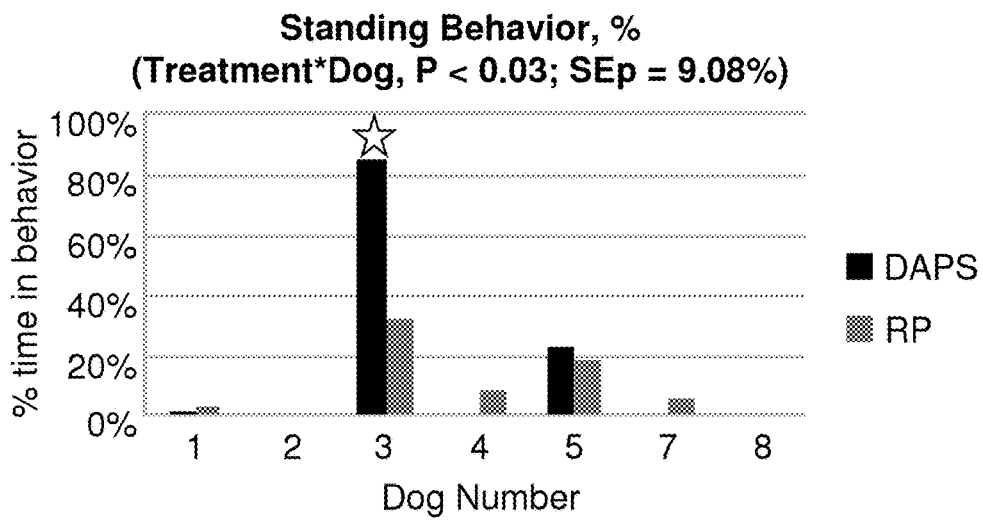
FIG. 12 is a graphic representation of effects of DAPS and RP in spray form on dog standing behavior.

While treatment by hour interaction was not significant for any behavior, the treatment by dog interaction was significant (P<0.05) for four behaviors. In Study 3, dogs 1 and 4 had increased pacing-walking after being given rabbit pheromone (FIG. 11). This is a partial replication of Study 1 (FIG. 3A) in that the RP spray also increased pacing-walking of dog 1 compared with the DAP collar. Dog 3 showed increased pacing-walking (FIG. 11) and increased standing (FIG. 12) in Study 3 when sprayed with DAP. In contrast, dog 3 showed increased sitting but not standing or pacing-walking in Study 1 when given the DAP collar.

Figure 13:
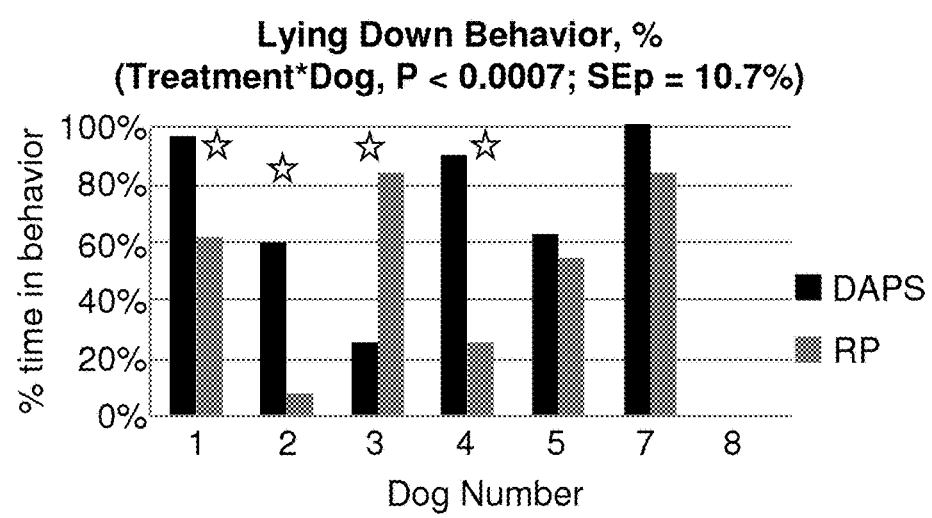
FIG. 13 is a graphic representation of effects of DAPS and RP in spray form on lying down behavior after startle.

Comparing rabbit pheromone spray with DAP spray during startle, it was noted that DAP spray increased lying down for dogs 1, 2, and 4 compared with rabbit pheromone (FIG. 13). Dog 3 showed increased lying down with rabbit pheromone spray compared with DAP spray.

Figure 14:
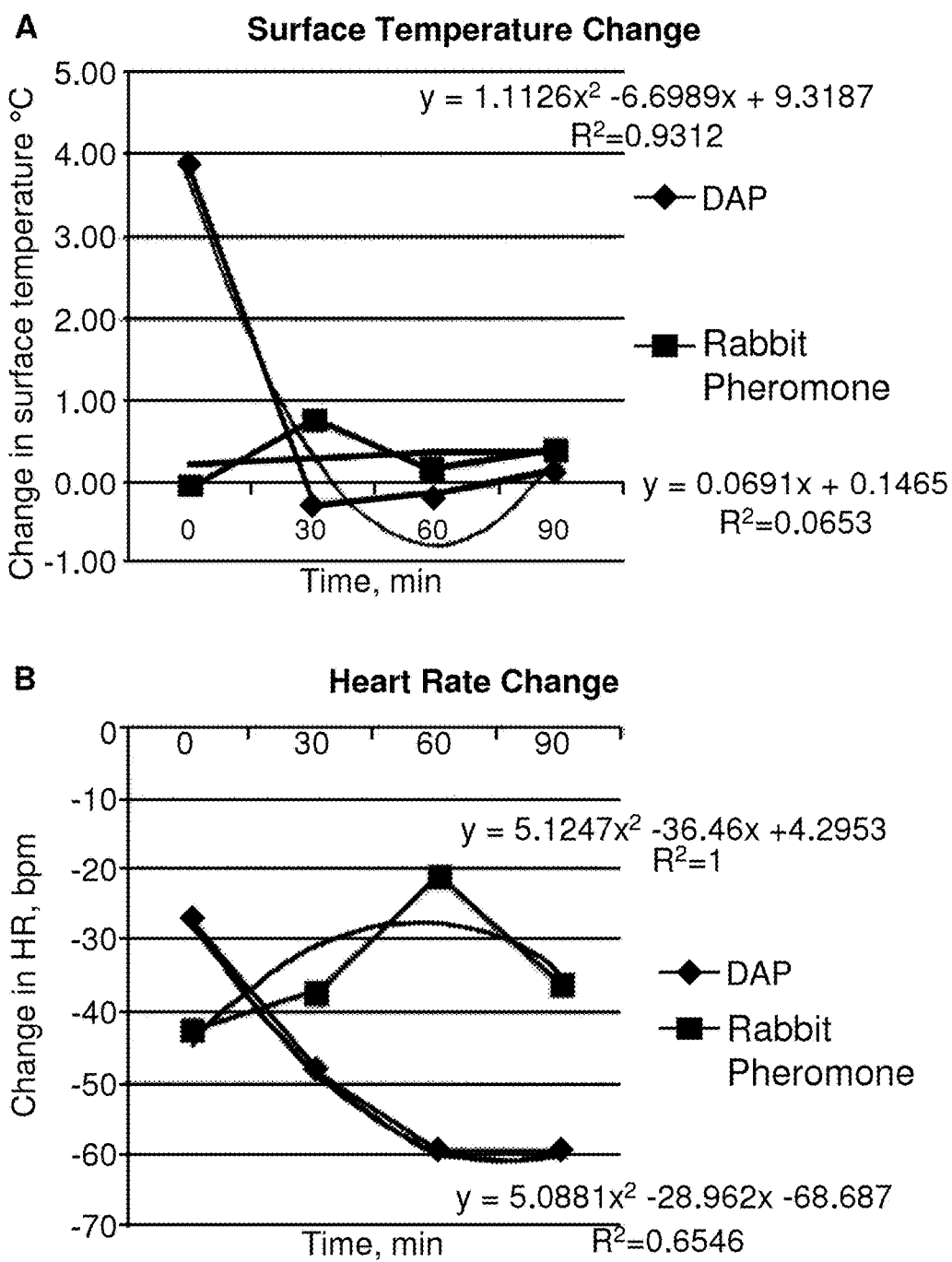
FIG. 14 is a graphic representation of change in surface temperature (FIG. 14A) and heart rate (FIG. 14B) of dogs 1-4 during each 30 minutes compared to the 30 minute period before startle. (Time 0=0-30 min; 30=30-60 min, 60=60-90 min and 90=90-120 min after startle).

Results as to Heart Rate:

Surface temperatures and heart rates of dogs given rabbit pheromone spray or DAP spray are presented in FIG. 14. DAP spray and startle caused an immediate increase in surface temperature of about 4° C. (See, FIG. 14A). After that, the surface temperature declined among DAP sprayed dogs and equaled that of rabbit pheromone sprayed dogs for 30, 60 and 90 minutes after startle.

The basal heart rates declined for all dogs. In FIG. 14B, data were presented as a change relative to time zero heart rate values. As seen in FIG. 14B, all the negative values demonstrated that heart rates declined. Heart rates were generally unchanged over time, although were lower than baseline rate, for dogs sprayed with the rabbit pheromone (FIG. 14B). Heart rates declined for dogs sprayed with DAPS and startled.

Integrating Behavior and Heart Rate in Study 3:

As seen in study 2, heart rates declined after startle. The decline in heart rate was associated, in some dogs, with an increase in lying down or sitting. Dog behavior generally reflected the heart rate data.

Study 4

In Study 4, putative pheromones were examined as room diffusers. Room diffusers were obtained and different liquid odors were applied over a 24 hour period. In contrast to Studies 1, 2, and 3, heart rates and behavior data were obtained over 24 hours (rather than just 2 hours after treatment application as in the other studies) and a baseline day was included in the dataset. Similar to Studies 1, 2, and 3, each dog experienced each treatment on different days in random order. The following treatment groups were evaluated: Baseline, Placebo Formula H Pheromone (SERG), DAP room diffuser (DAPRD; as available commercially) and the Rabbit Pheromone in diffuser form prepared in accordance with Example 4 (RPRD, 1 μg/mL). The baseline day data were first collected and then treatments were randomly assigned to dogs on a rotating basis until all dogs experienced all treatments.

Figure 15:
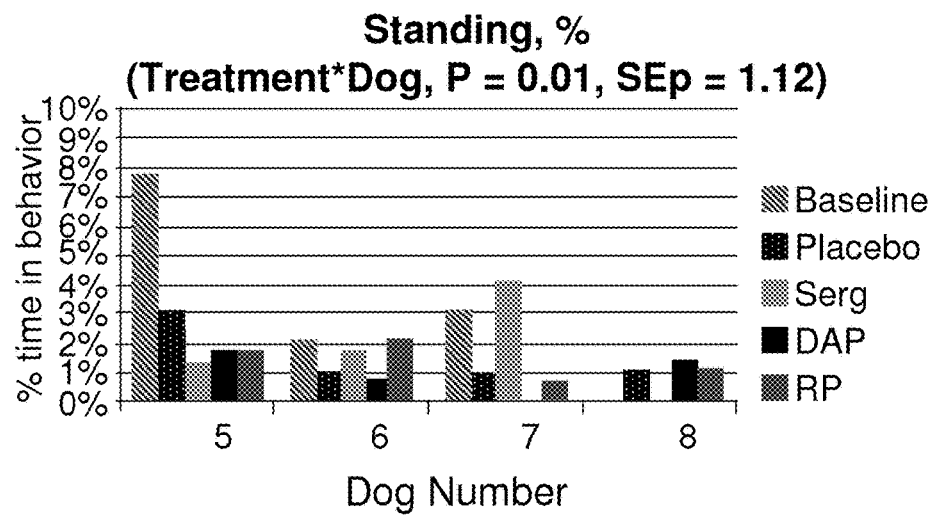
FIG. 15 is a graphic representation of effects of odors delivered by room diffuser on standing behavior of dogs 5-8.
Figure 16:
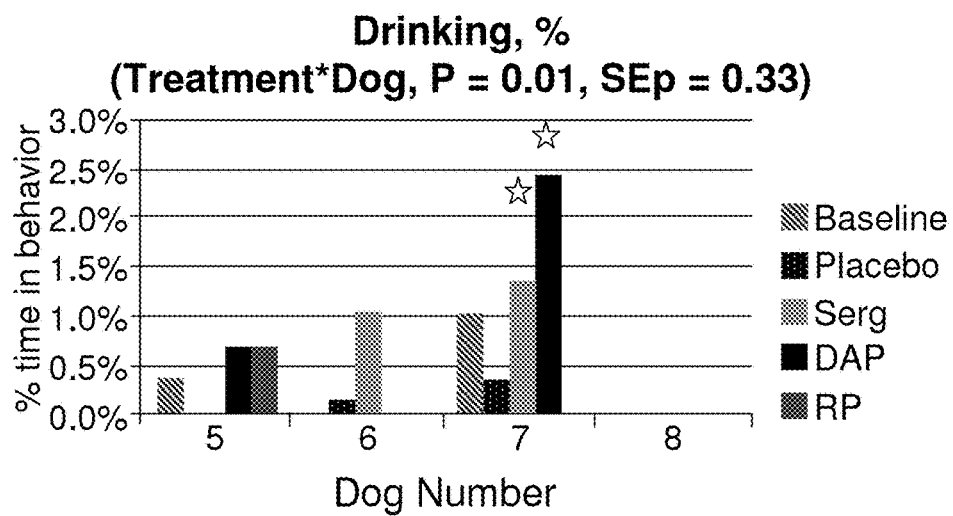
FIG. 16 is a graphic representation of effects of odors delivered by room diffuser on drinking behavior of dogs 5-8.

Results as to Behavior:

Fewer significant behavioral effects were observed in this study than in the previous studies (Table 11). The treatment by dog interaction was significant for standing and drinking behaviors (FIGS. 15 and 16). For standing behaviors, all treatment groups had lower (P<0.01) standing compared with baseline (FIG. 15). For drinking behavior, dog 7 showed increased drinking when it experienced Serg or RP room diffuser (FIG. 16). DAP's effect on increased drinking (and urination) was also found in some dogs.

TABLE 11

Dog Behavior under Room Diffuser (% of time)

| Behavior | Baseline | Placebo | SERG | DAP | RP | SE | TRT | Trt*Dog | Trt*Hr |
|---|---|---|---|---|---|---|---|---|---|
| Pace-Walk | 5.08% | 7.67% | 3.58% | 5.08% | 5.67% | 1.03% | 0.15 | 0.18 | 0.85 |
| Standing | 3.25% | 1.55% | 1.83% | 0.95% | 1.42% | 0.82% | 0.38 | 0.01 | 0.63 |
| Sitting | 7.46% | 6.13% | 4.08% | 4.75% | 5.00% | 1.31% | 0.43 | 0.28 | 0.81 |
| Lying Down | 83.1% | 84.2% | 88.9% | 87.0% | 87.0% | 2.0% | 0.30 | 0.15 | 0.87 |
| Lick self | 0.00% | 0.09% | 0.00% | 0.00% | 0.09% | 0.05% | 0.46 | 0.70 | 0.47 |
| Eat | 0.62% | 0.17% | 0.78% | 0.69% | 0.26% | 0.26% | 0.48 | 0.41 | 0.002* |
| Drink | 0.35% | 0.12% | 0.61% | 0.78% | 0.18% | 0.28% | 0.42 | 0.007 | 0.52 |
| Defecate | 0.00% | 0.00% | 0.12% | 0.18% | 0.18% | 0.11% | 0.64 | 0.10 | 0.42 |
| Urinate | 0.09% | 0.09% | 0.17% | 0.43% | 0.26% | 0.13% | 0.35 | 0.44 | 0.35 |

The significant (P<0.002) treatment by hour effect for eating (Table 11) is simply explained by the time required to feed and care for each dog. Because some dogs' eating fell into the next hour, the treatment by hour effect was significant only for eating. All other behaviors were consistent over time. Few behavioral effects and interactions were observed.

Results as to Heart Rate and Surface Temperature: Heart rate data main effects are presented in Table 12. Room diffuser treatments did not impact overall dog heart rates. Dog 5 had elevated heart rate and lower surface temperatures compared with dogs 6, 7, and 8 (Table 12).

TABLE 12

Dogs Overall Heart Rate and Surface Temperatures after Room Diffuser Treatment

| TREATMENT | HR | TEMP |
|---|---|---|
| Baseline | 80.9 | 34.7 |
| Placebo | 79.6 | 30.9 |
| Form H | 87.2 | 33.0 |
| DAP | 101.7 | 34.4 |

TABLE 12-continued

Dogs Overall Heart Rate and Surface
Temperatures after Room Diffuser Treatment

| RP | 108.4 | 33.8 |
| SEP | 14.9 | 1.14 |
| P-value | 0.58 | 0.21 |

| DOG NUMBER | HR | TEMP |
| --- | --- | --- |
| 5 | 140.6a | 30.6a |
| 6 | 78.4 | 34.4 |
| 7 | 81.8 | 32.9 |
| 8 | 65.4 | 35.5 |
| SEP | 13.3 | 1.02 |
| P-value | 0.008 | 0.03 |

Figure 17:
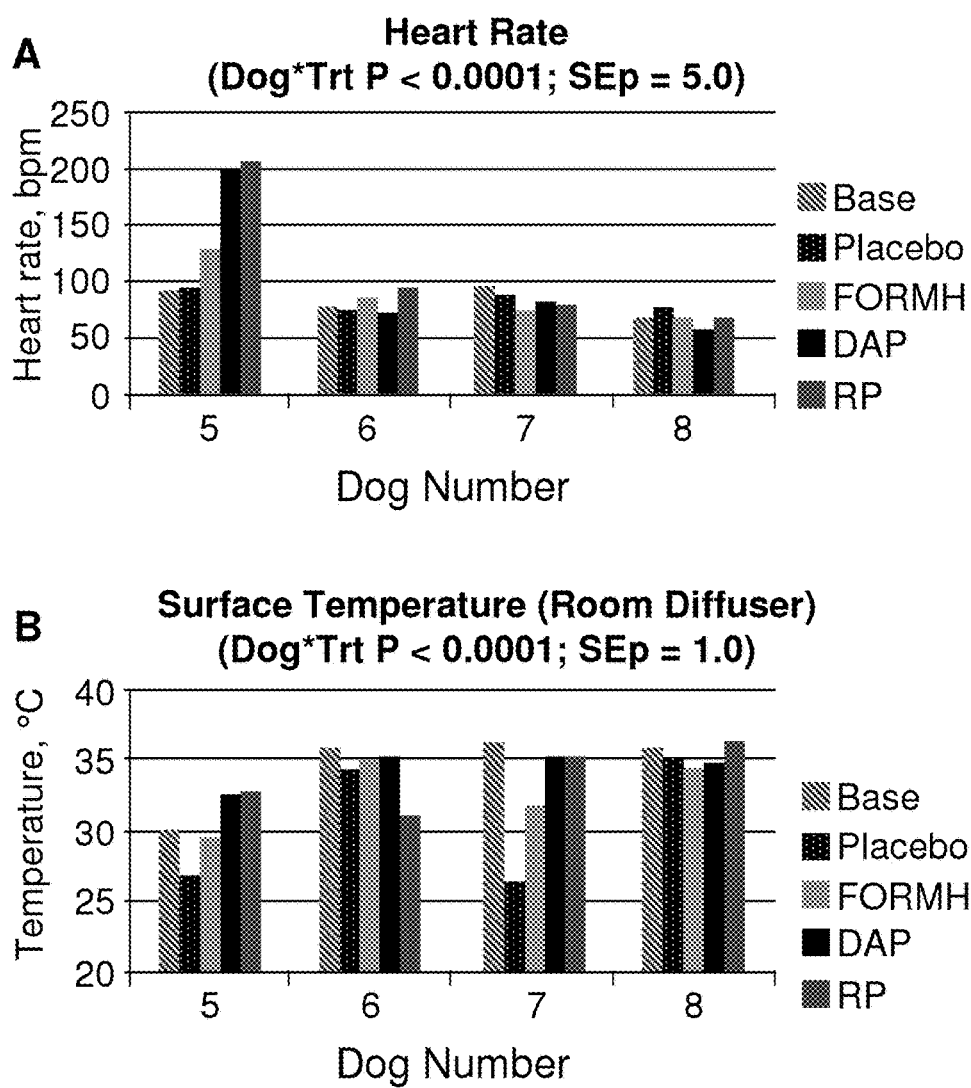
FIG. 17 is a graphic representation of heart rate (FIG. 17A) and surface temperature (FIG. 17B) of dogs 5-8 when room diffusers were used for 24 hours.

As shown in FIGS. 17A and 17B, the dog by treatment effect was highly significant (P>0.0001) for both heart rate (HR) and surface temperature. Dog 5 had elevated HR and surface temperature when exposed to DAP pheromone or rabbit pheromone room diffusers compared with the Placebo. Dog 6 had increased heart rate and decreased surface temperature with rabbit pheromone compared with the Placebo. Dog 7's heart rate was not impacted by treatment. However, DAP and RP increased the surface temperature of dog 7 compared to placebo. For Dog 8, both Serg and DAP reduced heart rate over the 24-hour period.

Integrating Behavior and Heart Rate in Study 4—Room Diffusers:

Dog 5 was the only dog most impacted by the Room Diffuser treatments applied. Its heart rate increased to about 200 bpm and its surface temperature increased between 2° C. to 5° C. when it experienced DAP or RP as a room diffuser (FIGS. 17A and 17B). Other effects on heart rate were much smaller in magnitude. Dog 7's increase in surface temperature, from RP or DAP room diffusers, was not correlated with any measured behavior change.

Overall Conclusions

Three delivery methods were examined (collar, spray, and room diffuser) and conclusions may be drawn about their efficacy. First, the pheromones were similar in efficacy when applied as a collar or spray. When used as a room diffuser, the pheromones/INTEROMONE® had fewer significant effects compared with when they were delivered in collar or spray form.

Figure 18:
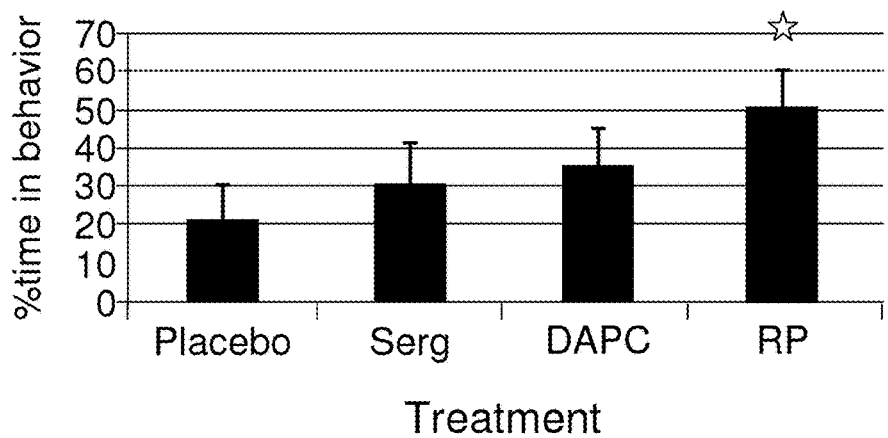
FIG. 18 is a graphic representation of results from a Meta-Analysis of three studies (Studies 1, 2, and 4) that included all 4 treatment groups.
Figure 18:
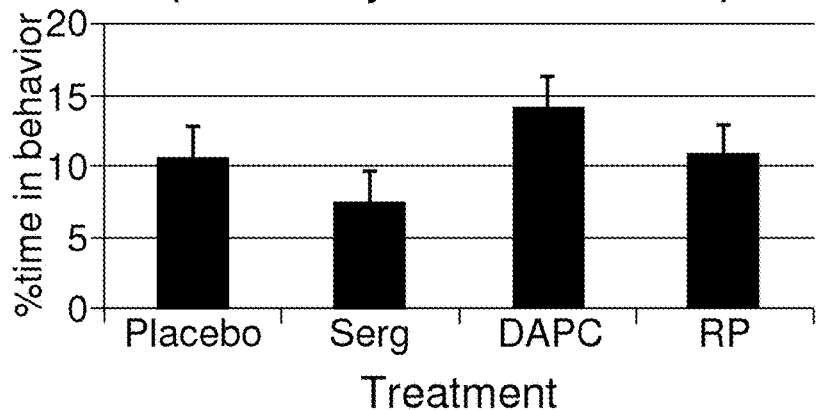

All four studies indicated that pheromones and INTEROMONE® have significant effects on the physiology and behavior of dogs. Meta-analyses were performed across studies to identify potential over-arching effects (FIGS. 18A and B). Only dog sitting behavior was increased by the use of rabbit INTEROMONE®. The reaction of most dogs to handling or startle was to go lay down; but the dogs exposed to rabbit INTEROMONE® were more likely to sit. Other than this general effect, each other finding must be considered within the context of the form of delivery (spray, collar or room diffuser) and the response of individual dog.

It was notable that no dog licked itself during the baseline period or under placebo in Study 1 (Tables 7 and 8). When dogs were startled in Study 2, the placebo dogs licked themselves (Table 9), but dogs in each treatment group had "lick self" values of zero. Therefore, one could conclude that each pheromone or INTEROMONE® reduced or eliminated startle-induced licking of self in dogs.

Dogs 3, 5, and 7 paced during the baseline data collection. They averaged from 19% to 50% of their time pacing (Table 7) while the other five dogs did not pace during baseline data collection. Dog 1 began pacing at a high rate when exposed to DAP (FIG. 3A). Dog 3 increased pacing with Serg, but reduced its pacing with DAP collar and rabbit INTEROMONE® spray. Dog 5 was largely unaffected by any pheromone/INTEROMONE®. Dog 7's pacing was reduced by DAP collar and reduced even more by rabbit INTEROMONE® spray (FIG. 3A).

Eating, drinking, urinating and defecating were highly correlated and dependent upon how the dogs were managed. Examination of these behaviors in Table 7 showed that only some dogs exhibited these behaviors. Only in Study 4 was the treatment by dog interaction significant for drinking behavior. DAP and Serg tended to increase dog water drinking when these pheromones were in room diffuser form or (in a non-significant way, but greater than zero) after dogs were startled.

Among the various pheromones, the rabbit INTEROMONE® had the most consistent or largest effect on dog behavior and physiology.

Example 7—Determining Efficacy of a Collar Containing Rabbit INTEROMONE® Compared to Pheromone Collars The objective of this study was to compare the efficacy of two pheromone collars (Ceva Dog Appeasing Pheromone Collar (DAP) and Sergeant's pheromone collar (Sentry or Meridian brands) with the new rabbit INTEROMONE® collar (prepared in accordance with Example 2) and all against a Placebo. Four male dogs were used as test subjects. Each dog was clinically diagnosed as "anxious" dogs by a veterinarian boarded in animal behavior (Dr. Valerie Tynes). Dogs were kept one per room. The rooms were spacious (10'6"×17'8"). Each dog had a water bowl, was fed once per day ad libitum and had access to at least one toy on a continual basis. Heart rate and surface temperature were measured by telemetry.

The study was conducted in two phases: Baseline and after startle. In the baseline study each of the four dogs received each collar treatment in random order for two days at a time. Heart rate and surface temperature were collected each 5 seconds for 24 hours. In the second phase, dogs were startled with a 110 dB Fog Horn and heart rate was measured each 1 second for 10 minutes before and 2 hours after startle.

Figure 19:
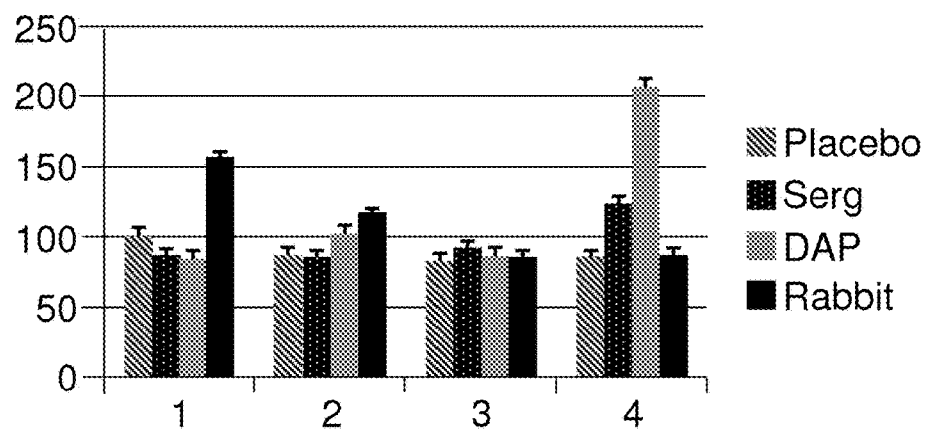
FIG. 19 is a graphic representation of the effects of placebo, SERG, DAP, or Rabbit pheromone collars on dog heart rate after 24 hours.
Figure 20:
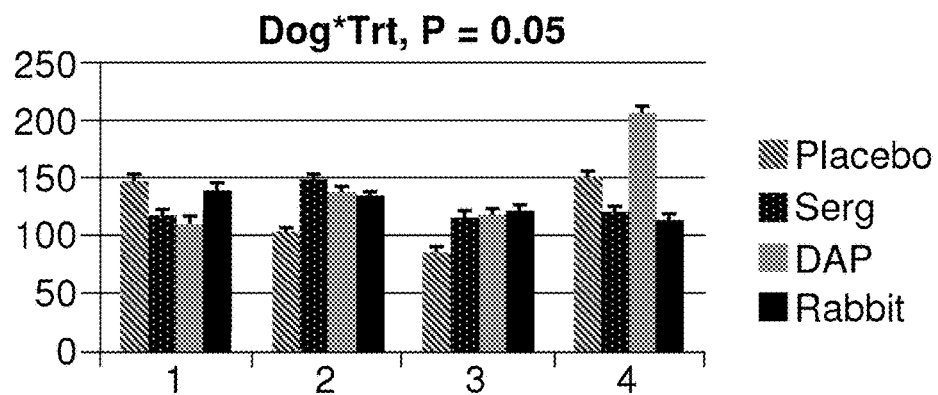
FIG. 20 is a graphic representation of the effects of placebo, SERG, DAP, or Rabbit pheromone collars on dog heart rate after startle.
Figure 21:
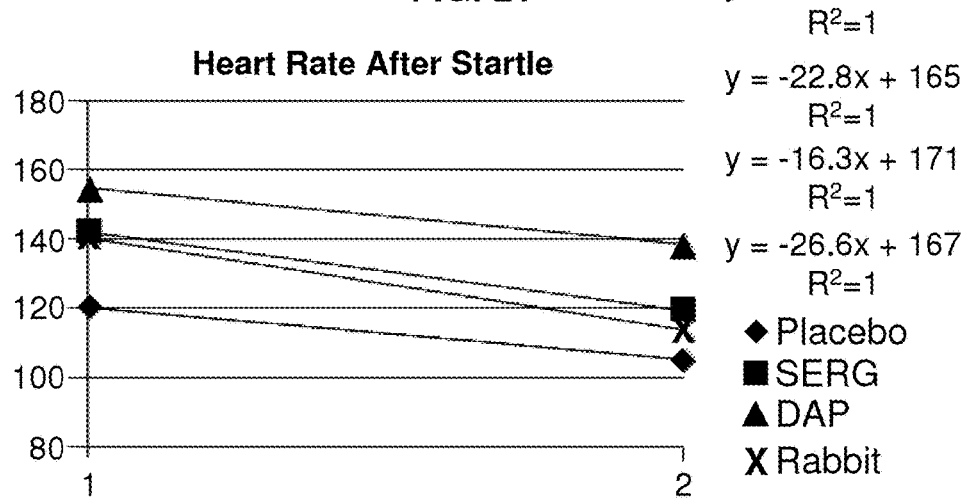
FIG. 21 is a graphic representation of the effects of placebo, SERG, DAP, or Rabbit pheromone collars on dog heart rate two hours after startle.

Heart rate data are presented in FIGS. 19-21. The overall heart rate data did not show a significant treatment effect. However, the Treatment by Dog interaction approached significance (P=0.10). These data are presented in FIG. 19. The data indicate that dogs' heart rates responded differently to treatments. The RP collar increased the heart rate of dog 1 and the DAP collar increased the heart rate of dog 4. The Sergeant's collar also increased the heart rate of dog 4 compared to Placebo, but less than with the DAP collar.

Dogs were startled with the Fog Horn. The startle typically increases heart rate and then it declines. The rate of decline is proportional to the degree to which the anxious dog benefitted from the pheromone/INTEROMONE®. FIG. 20 illustrates that Dog by Treatment interaction was significant (P=0.046). Dogs 1 and 4 had reduced heart rate from Serg and RP collars. DAP reduced heart rate only in dog 1. After startle, DAP significantly increased heart rate in dog 4.

FIG. 21 illustrates the rate of decline in heart rate in the hour of the startle (hour 1) and in the next hour (hour 2). The slope of the line (the value before the x in the regression equation) indicates the decline in heart rate. The placebocollared dogs' heart rate declined 15 beats per minute (bpm) and RP-collared dogs' heart rate declined 26.6 bpm.

Figure 22:
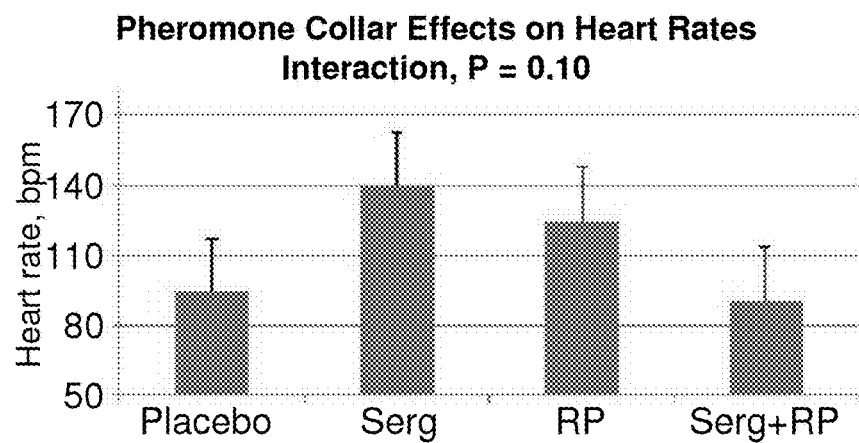
FIG. 22 is a graphic representation of the effects of pheromone collars on dog heart rate collected over 24 hours. The pheromone collars include placebo, Serg, RP, and a combination of Serg and RP.
Figure 23:
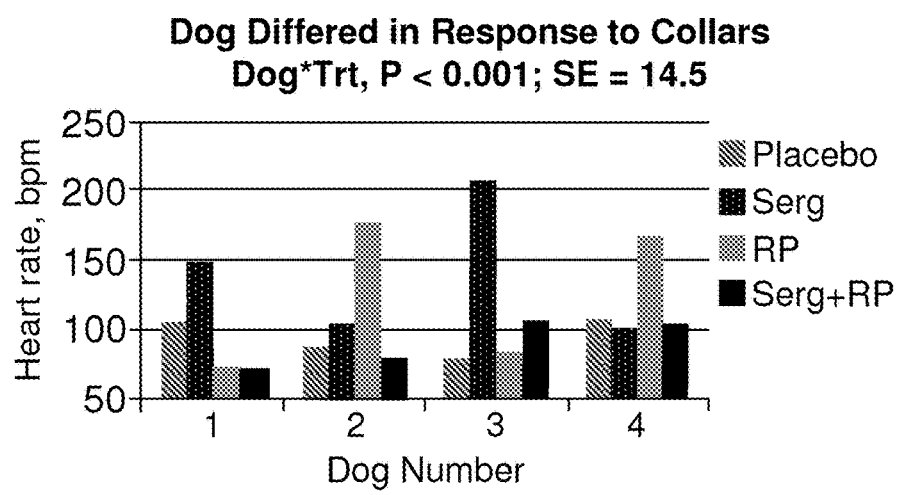
FIG. 23 is a graphic representation of the effect of each treatment collar on individual dogs. The pheromone collars include placebo, Serg, RP, and a combination of Serg and RP.

Example 8—Determining Efficacy of a Rabbit Pheromone as INTEROMONE® in a Collar to Modulate Heart Rate in Anxious Dogs Compared to a Pheromone Only Collar and an INTEROMONE®/Pheromone Combined Collar Dogs diagnosed as being "nervous" were treated with four different treatments on different days: Placebo collar, Pheromone only collar (Serg), Rabbit INTEROMONE® collar (RP), and INTEROMONE® Plus Pheromone collar (Serg+RP). Each dog experienced a given collar for 24 hours. Heart rate of the dogs was measured by remote telemetry. Data acquired during basal testing are presented in FIGS. 22 and 23. FIG. 22 illustrates the effects of the collars on heart rate collected over a period of 24 hours. Both Serg and RP increased heart rate, but the combined effect of Serg and RP was not different than the placebo.

Figure 24:
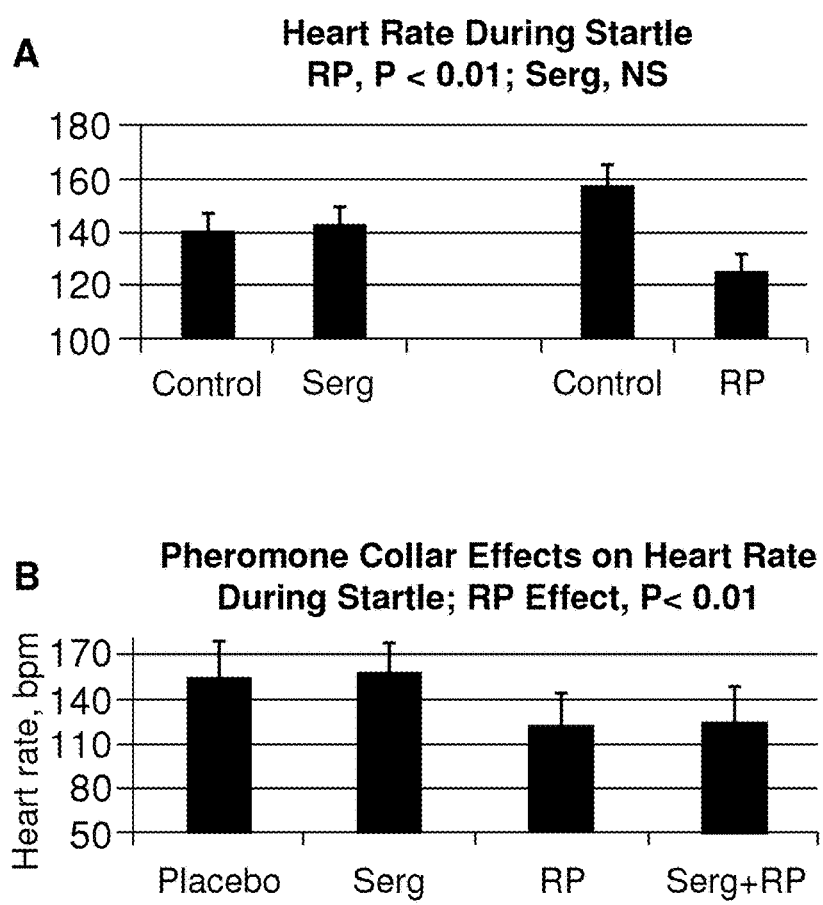
FIG. 24 is a graphic representation of the effects of pheromone collars on dog heart rate while startled.
Figure 25:
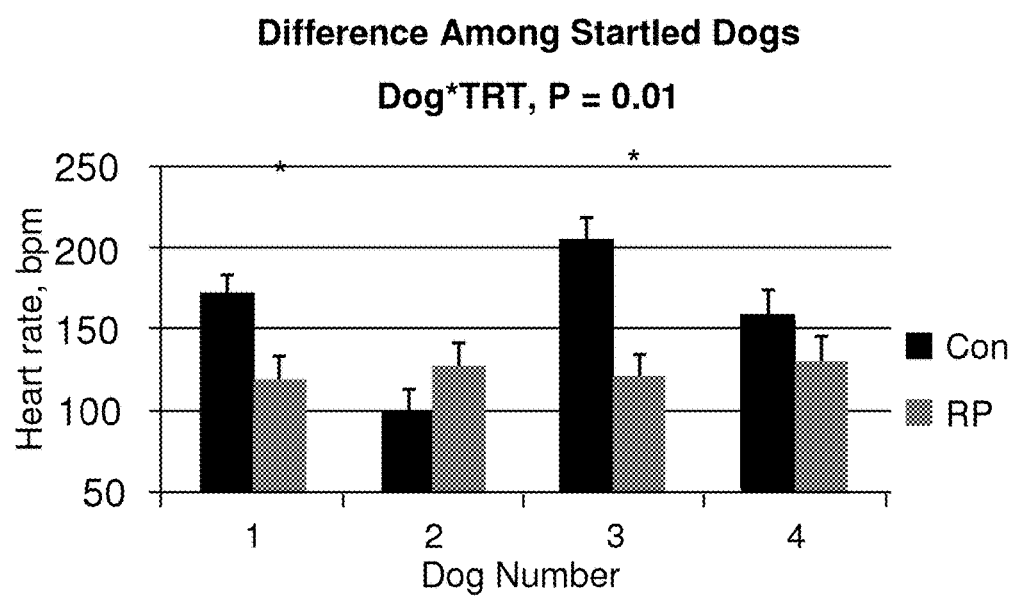
FIG. 25 is a graphic representation of the dog response to the RP collar.

Each dog experienced a loud noise (fog horn) during a 2 second blast. The noise startled the dogs. Each dog had the collar on before, during and after the startle experience. Data are summarized in FIGS. 24A, 24B and 25. FIG. 24A shows main effects of Serg and RP. Dogs with Serg collar did not differ from the control. Dogs with the RP collar had lower heart rate during startle compared to control dogs. The data illustrates that Serg alone had no effect on the startled dog heart rate. Either RP alone or with Serg had reduced heart rate. The data further indicate that only the RP is effective in reducing the heart rate of startled dogs.

Example 9—Determining Efficacy of Rabbit Pheromone as INTEROMONE® in a Collar to Modulate Heart Rate in Anxious Dogs The objective of this study was to assess efficacy of pheromones/INTEROMONE® to modulate heart rate and behavior in adult anxious dogs (trembling, cowering, shy). The dogs (8.1±0.18 kg; estimated 5-12 yr intact males) were obtained from a local research facility. Body weights and feed intake were recorded. Each dog was housed in a separately ventilated room with a minimum of 12 m$^2$ of floor space. Heart rate (HR) and surface temperature was measured using a telemetry system (Data Science International, St. Paul, Minn.). Behavior was recorded on a DVR and later reviewed by a trained individual. A scan sample was used with a recording interval of 5 min over 24 hours.

The dogs were treated with four different treatments on different days: Placebo collar (no Pheromone/INTEROMONE®), Pheromone only collar (SERG), Rabbit pheromone as INTEROMONE® collar (RP), and INTEROMONE® plus Pheromone collar (SERG+RP). At the end of 24 hours with a given collar, each dog was startled with a 110 db foghorn placed 12 cm from the dog's head while behavior and heart rate were recorded. Each dog received each treatment in a Latin square design with repeated measures over time. This model allowed evaluation of effects of treatment, dog, treatment by dog, time, treatment by time and dog by time.

Baseline HR did not differ among treatments (avg=110.1±13.3 bpm). After startle, the RP lowered (P<0.01) HR compared with placebo (124.5±7.2 vs. 157.8±7.2 bpm); however, the treatment by dog interaction (P<0.01) indicated certain dogs were more responsive than others. Dogs with RP collars spent more time lying down (87.4±5.4 vs. 63.2±4.8% of time, P=0.01) and less time pacing (3.0±0.2 vs. 3.8±0.02%, P<0.05) than placebo-treated dogs. Pace/walk changed differentially among treatments and dogs (dog by RP and SERG effects for pace/walk, P=0.05).

In summary, RP lowered HR while SERG and SERG+RP did not change dog HR. However, pheromone/INTEROMONE® treatments had differential effects on individual dog behavior and HR. Pheromones/INTEROMONE® can cause meaningful changes in dog behavior and HR among certain anxious dogs.

Example 10—Administration of a Collar Containing 2-methylbut-2-enal to Cats

A collar containing 2-methylbut-2-enal can be prepared in accordance with Example 3. The resultant collar, when worn by a cat, will cause the cat to exhibit a significant change in behavior towards a calmer demeanor.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method of modifying behavior in an animal, the method comprising: administering a composition to the animal for a period of time, the composition comprising between about 0.001% and about 1% (w/w) 2-methylbut-2-enal and between about 0.5% and 99.99% (w/w) of at least one solvent, wherein the animal is a dog or a cat, and wherein anxiety, stress, and aggressiveness in the animal is reduced.

2. The method of claim 1, wherein the method of administration is inhalation.

3. The method of claim 1, wherein the composition is formulated as a spray, a diffuser, or a slow release matrix.

4. The method of claim 3, wherein administering the spray composition comprises spraying the animal or spraying the animal's environment with the composition.

5. The method of claim 1, wherein the period of time is at least one second.

6. The method of claim 1, wherein the period of time is at least one week.

7. The method of claim 1, wherein the period of time is at least one month.

8. The method of claim 1, wherein the composition comprises at least one additional pheromone or pheromone composition.

9. A method of modifying behavior in an animal, the method comprising: administering an effective amount of a spray composition to the animal for a period of time, the spray composition comprising about 0.01% (w/w) 2-methylbut-2-enal, about 10% (w/w) isopropyl alcohol, and about 89.49% (w/w) water, wherein the animal is a dog or a cat, and wherein anxiety, stress, and aggressiveness in the animal is reduced.

10. A method of modifying behavior in an animal, the method comprising: administering an effective amount of a diffuser composition to the animal for a period of time, the diffuser composition comprising about 0.02% (w/w) 2-methylbut-2-enal, about 15% (w/w) isopropyl palmitate, and about 84.48% (w/w) silicone fluid, wherein the animal is a dog or a cat, and wherein anxiety, stress, and aggressiveness in the animal is reduced.

11. A method of modifying behavior in an animal, the method comprising: administering an effective amount of a slow release matrix composition to the animal for a period of time, the slow release matrix composition comprising about 0.02% (w/w) 2-methylbut-2-enal, and about 99.780% (w/w) copolymer, wherein the animal is a dog or a cat, and wherein anxiety, stress, and aggressiveness in the animal is reduced.

12. The method of claim 1, wherein the animal is a dog.

13. A method of calming an animal, the method comprising: administering a composition to the animal for a period of time, the composition comprising between about 0.001% and about 1% (w/w) of 2-methylbut-2-enal and between about 0.5% and 99.99% (w/w) of at least one carrier solvent, wherein the animal is a dog or a cat.

* * * * *